(12) United States Patent
Ishii et al.

(10) Patent No.: US 10,336,772 B2
(45) Date of Patent: *Jul. 2, 2019

(54) BICARBAZOLE COMPOUND, MATERIAL FOR ORGANIC LIGHT-EMITTING DEVICE INCLUDING BICARBAZOLE COMPOUND, AND ORGANIC LIGHT-EMITTING DEVICE INCLUDING BICARBAZOLE COMPOUND

(71) Applicant: SAMSUNG ELECTRONICS CO., LTD., Suwon-si, Gyeonggi-do (KR)

(72) Inventors: Norihito Ishii, Yokohama (JP); Katsunori Shibata, Yokohama (JP); Satoshi Inayama, Yokohama (JP); Mitsunori Ito, Yokohama (JP)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 218 days.

This patent is subject to a terminal disclaimer.

(21) Appl. No.: 15/391,574

(22) Filed: Dec. 27, 2016

(65) Prior Publication Data

US 2017/0183360 A1    Jun. 29, 2017

(30) Foreign Application Priority Data

Dec. 28, 2015  (JP) ................. 2015-257233
Nov. 28, 2016  (KR) ............ 10-2016-0159417

(51) Int. Cl.
| | | |
|---|---|---|
| *H01L 51/00* | (2006.01) | |
| *H01L 51/50* | (2006.01) | |
| *C07D 498/06* | (2006.01) | |

(52) U.S. Cl.
CPC ........ *C07D 498/06* (2013.01); *H01L 51/0072* (2013.01); *H01L 51/5004* (2013.01); *H01L 51/5016* (2013.01)

(58) Field of Classification Search
CPC .............. C07D 498/06; H01L 51/0072; H01L 51/5004; H01L 51/5016
See application file for complete search history.

(56) References Cited

U.S. PATENT DOCUMENTS

| | | | |
|---|---|---|---|
| 2009/0295275 A1* | 12/2009 | Parham | ................ C07D 471/16 313/504 |
| 2012/0319052 A1 | 12/2012 | Brocke et al. | |
| 2014/0058099 A1 | 2/2014 | Wakamiya et al. | |
| 2015/0179955 A1 | 6/2015 | Miyata | |
| 2015/0236274 A1 | 8/2015 | Hatakeyama et al. | |
| 2016/0126476 A1* | 5/2016 | Choi | .................... C07D 455/04 257/40 |

FOREIGN PATENT DOCUMENTS

| | | | |
|---|---|---|---|
| JP | 2009-512628 A | 3/2009 | |
| JP | 2012-507507 A | 3/2012 | |
| JP | 2013-521238 A | 6/2013 | |
| JP | 2015-122384 A | 7/2015 | |
| KR | 10-2015-0137266 | * 12/2015 | |
| WO | 2011-107186 A2 | 9/2011 | |
| WO | 2012-118164 A1 | 9/2012 | |
| WO | WO-2014119895 A1 * | 8/2014 | ........... C07D 455/04 |
| WO | 2015-102118 A1 | 7/2015 | |

OTHER PUBLICATIONS

Machine translation for KR 10-2015-0137266 (publication date: Dec. 2015). (Year: 2015).*

* cited by examiner

*Primary Examiner* — Dawn L Garrett
(74) *Attorney, Agent, or Firm* — Cantor Colburn LLP

(57) ABSTRACT

A bicarbazole compound represented by Formula 1:

$$[Ar_1]_{n1}\text{-}(L_1)_{a1}\text{-}[Ar_2]_{n2} \qquad \text{Formula 1}$$

wherein in Formula 1, a1, $Ar_1$, $Ar_2$, $L_1$, n1, and n2 are the same as described in the specification.

13 Claims, 1 Drawing Sheet

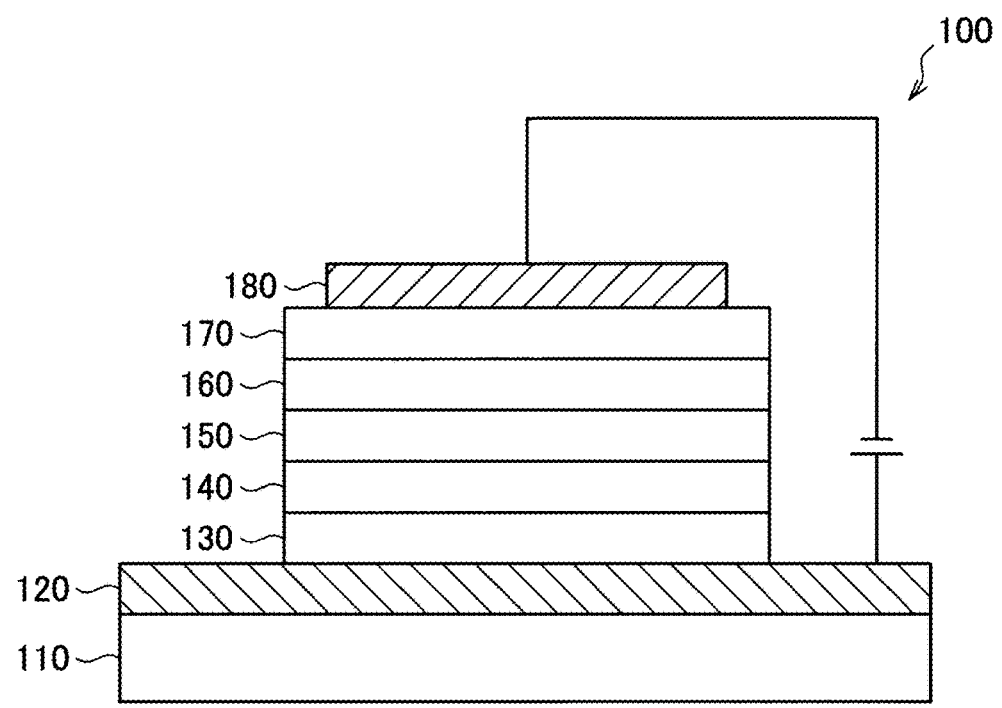

BICARBAZOLE COMPOUND, MATERIAL FOR ORGANIC LIGHT-EMITTING DEVICE INCLUDING BICARBAZOLE COMPOUND, AND ORGANIC LIGHT-EMITTING DEVICE INCLUDING BICARBAZOLE COMPOUND

CROSS-REFERENCE TO RELATED APPLICATIONS

This application claims priority to Japanese Patent Application No. 2015-257233, filed on Dec. 28, 2015, in the Japanese Patent Office, and Korean Patent Application No. 10-2016-0159417, filed on Nov. 28, 2016, in the Korean Intellectual Property Office, and all the benefits accruing therefrom under 35 U.S.C. § 119, the contents of which are incorporated herein in their entirety by reference.

BACKGROUND

1. Field

The present disclosure relates to a bicarbazole compound, a material for an organic light-emitting device including the bicarbazole compound, and an organic light-emitting device including the bicarbazole compound.

2. Description of the Related Art

Organic light-emitting devices (OLEDs) are self-emission devices that have wide viewing angles, high contrast ratios, and short response times. In addition, the OLEDs exhibit high luminance, driving voltage, and response speed characteristics, and produce full-color images.

Typical OLEDs include an anode, a cathode, and an organic layer that is disposed between the anode and the cathode, wherein the organic layer includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. Carriers, such as holes and electrons, recombine in the emission layer to produce excitons. These excitons transition from an excited state to a ground state to thereby generate light.

Various types of organic light emitting devices are known. However, there still remains a need in OLEDs having low driving voltage, high efficiency, high brightness, and long lifespan.

SUMMARY

Provided is a bicarbazole compound.

Provided is a material for an organic light-emitting device including the bicarbazole compound.

Provided is an organic light-emitting device including the bicarbazole compound.

Additional aspects will be set forth in part in the description which follows and, in part, will be apparent from the description, or may be learned by practice of the presented embodiments.

According to an aspect of an embodiment, a bicarbazole compound is represented by Formula 1:

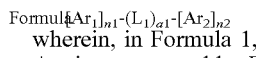

wherein, in Formula 1,
Ar$_1$ is represented by Formula 1A:

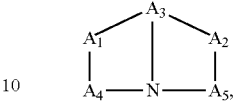

Formula 1A wherein, in Formula 1A,
A$_1$ and A$_2$ are each independently selected from a single bond, a substituted or unsubstituted C$_1$-C$_{10}$ alkylene group, a substituted or unsubstituted C$_1$-C$_{10}$ alkylsilylene group, a substituted or unsubstituted arylsilylene group having 6 to 30 ring-forming atoms, a substituted or unsubstituted aryl group having 6 to 30 ring-forming atoms, a substituted or unsubstituted heteroarylene group having 5 to 30 ring-forming atoms, O, and S, provided that at least one selected from A$_1$ and A$_2$ is selected from a substituted or unsubstituted C$_1$-C$_{10}$ alkylene group, a substituted or unsubstituted C$_1$-C$_{10}$ alkylsilylene group, a substituted or unsubstituted arylsilylene group having 6 to 30 ring-forming atoms, a substituted or unsubstituted aryl group having 6 to 30 ring-forming atoms, a substituted or unsubstituted heteroarylene group having 5 to 30 ring-forming atoms, O, and S, A$_3$ is selected from a substituted or unsubstituted C$_1$-C$_{10}$ trivalent alkyl group, a substituted or unsubstituted trivalent aryl group having 6 to 30 ring-forming atoms, and a substituted or unsubstituted trivalent heteroaryl group having 5 to 30 ring-forming atoms, A$_4$ and A$_5$ are each independently selected from a substituted or unsubstituted C$_1$-C$_{10}$ alkylene group, a substituted or unsubstituted aryl group having 6 to 30 ring-forming atoms, and a substituted or unsubstituted heteroarylene group having 5 to 30 ring-forming atoms, A$_4$ and A$_5$ are optionally bound via a single bond, O, S, a substituted or unsubstituted C$_1$-C$_{10}$ alkylsilylene group, a substituted or unsubstituted arylsilylene group having 6 to 30 ring-forming atoms, or a crosslinking group, Ar$_2$ is represented by Formula 1B:

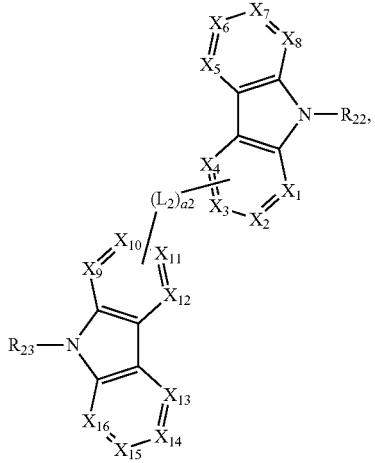

Formula 1B wherein, in Formula 1B,
X$_1$ to X$_{16}$ are each independently selected from a nitrogen atom and CR$_{21}$,
R$_{21}$ is selected from a binding site to L$_1$, a binding site to L$_2$, hydrogen, a deuterium atom, a substituted or unsubstituted $C_1$-$C_{10}$ alkyl group, a substituted or unsubstituted aryl group having 6 to 30 ring-forming atoms, and a substituted or unsubstituted heteroaryl group having 5 to 30 ring-forming atoms, $R_{21}$ is optionally bound to adjacent $R_{21}$ to form a condensed ring, two substituents of $X_1$ to $X_{16}$ each have a C-($L_2$-binding site) structure, $R_{22}$ and $R_{23}$ are each independently selected from a binding site to $L_1$, a substituted or unsubstituted aryl group having 6 to 30 ring-forming atoms, and a substituted or unsubstituted heteroaryl group having 5 to 30 ring-forming atoms, at least one selected from $R_{21}$ to $R_{23}$ is a binding site to $L_1$, n1 and n2 are each independently an integer from 1 to 20, $L_1$ and $L_2$ are each independently selected from a single bond and a substituted or unsubstituted arylene group having 6 to 30 ring-forming atoms, and a1 and a2 are each independently an integer from 0 to 3.

According to an aspect of another embodiment, a material for an organic light-emitting device includes the bicarbazole compound represented by Formula 1.

According to an aspect of still another embodiment, an organic light-emitting device includes:

a first electrode;

a second electrode; and an organic layer disposed between the first electrode and the second electrode, wherein the organic layer includes an emission layer and at least one bicarbazole compound represented by Formula 1.

BRIEF DESCRIPTION OF THE DRAWINGS

These and/or other aspects will become apparent and more readily appreciated from the following description of the embodiments, taken in conjunction with the accompanying drawings in which:

FIGURE is a schematic cross-sectional view illustrating an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

One or more embodiments of the inventive concept of the present disclosure will now be described more fully with reference to the accompanying drawings. In addition, in the present specification and drawings, like reference numerals in the drawings denote like elements, and thus, their description will be omitted.

In the present specification, the "alkyl group" may refer to a linear or branched aliphatic saturated hydrocarbon monovalent group having a specified number of carbon atoms. The "alkyl group" may be a linear or branched alkyl group. Examples of the alkyl group include a methyl group, an ethyl group, a propyl group; an iso-propyl group, an n-butyl group, a sec-butyl group, an iso-butyl group, a t-butyl group, an n-pentyl group, an n-hexyl group, an n-heptyl group, and an n-octyl group.

In the present specification, the "aryl group" may refer to a monovalent group having an aromatic system having a specified number of carbon atoms. The "aryl group" may be a monocyclic aromatic group or a condensed polycyclic aromatic group. Examples of the aryl group include a phenyl group, a naphthyl group, an anthryl group, a phenanthryl group, a naphthacenyl group, a pyrenyl group, a biphenylyl group, a terphenyl group, a tolyl group, a fluoranthenyl group, and a fluorenyl group.

In the present specification, the "heteroaryl group" may refer to a monovalent group having a heterocyclic aromatic system that has at least one heteroatom selected from N, O, P, and S as a ring-forming atom, and a specified number of carbon atoms. The "heteroaryl group" may be a monocyclic aromatic group or a condensed polycyclic aromatic group. Examples of the heteroaryl group include a pyrrolyl group, a pyridinyl group, a pyrazinyl group, an indolyl group, an isoindolyl group, a triazinyl group, a furyl group, a benzofuranyl group, an isobenzofuranyl group, a quinolyl group, an isoquinolyl group, a quinoxalinyl group, a carbazolyl group, a phenanthridinyl group, an acridinyl group, a phenazinyl group, a phenothiazinyl group, a phenoxazinyl group, an oxazolyl group, an oxadiazolyl group, a furazanyl group, a thienyl group, a dibenzofuranyl group, and a dibenzothienyl group, In the present specification, an alkylene group, an arylene group, and a heteroarylene group each refer to a divalent substituent in which a hydrogen atom is further removed from the alkyl group, the aryl group, and the heteroaryl group, respectively, In the present specification, a trivalent alkyl group, a trivalent aryl group, and a trivalent heteroaryl group each refer to a trivalent substituent in which two hydrogen atoms are further removed from the alkyl group, the aryl group, and the heteroaryl group, respectively.

In the present specification, the term "substituted" means that a group is substituted with any substituent, and more particularly means that a group is substituted with the alkyl group, the aryl group, or the heteroaryl group.

When a group containing a specified number of carbon atoms is substituted with any of the groups listed in the preceding paragraph, the number of carbon atoms in the resulting "substituted" group is defined as the sum of the carbon atoms contained in the original (unsubstituted) group and the carbon atoms (if any) contained in the substituent. For example, when the term "substituted C1-C30 alkyl" refers to a C1-C30 alkyl group substituted with C6-C30 aryl group, the total number of carbon atoms in the resulting aryl substituted alkyl group is C7-C60.

Bicarbazole Compound

A bicarbazole compound may be represented by Formula 1:

                                      Formula 1

In Formula 1, $Ar_1$, n1, $L_1$, a1, $Ar_2$, and n2 may be the same as those described herein.

In Formula 1, $Ar_1$ may be represented by Formula 1A:

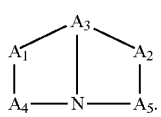                                      Formula 1A

In Formula 1A, $A_1$ and $A_2$ may each independently be selected from a single bond, a substituted or unsubstituted $C_1$-$C_{10}$ alkylene group, a substituted or unsubstituted $C_1$-$C_{10}$ alkylsilylene group, a substituted or unsubstituted arylsilylene group having 6 to 30 ring-forming atoms, a substituted or unsubstituted aryl group having 6 to 30 ring-forming atoms, a substituted or unsubstituted heteroarylene group having 5 to 30 ring-forming atoms, O, and S, provided that at least one selected from $A_1$ and $A_2$ may be selected from a substituted or unsubstituted $C_1$-$C_{10}$ alkylene group, a substituted or unsubstituted $C_1$-$C_{10}$ alkylsilylene group, a substituted or unsubstituted arylsilylene group having 6 to 30 ring-forming atoms, a substituted or unsubstituted aryl group having 6 to 30 ring-forming atoms, a substituted or unsubstituted heteroarylene group having 5 to 30 ring-forming atoms, O, and S.

In Formula 1A, when both of $A_1$ and $A_2$ are a single bond, basicity or electron donating properties of "N" in Formula 1A may be reduced. In this case, properties of the bicarbazole compound represented by Formula 1 as a hole transport host may be deteriorated. Accordingly, it is not desirable that both of $A_1$ and $A_2$ are a single bond.

In some embodiments, in Formula 1A, $A_1$ and $A_2$ may each independently be selected from a single bond, a substituted or unsubstituted $C_1$-$C_5$ alkylene group, a substituted or unsubstituted $C_1$-$C_{10}$ alkylsilylene group, a substituted or unsubstituted arylsilylene group having 6 to 30 ring-forming atoms, O, and S, and at least one selected from $A_1$ and $A_2$ may be selected from a substituted or unsubstituted $C_1$-$C_5$ alkylene group, a substituted or unsubstituted $C_1$-$C_{10}$ alkylsilylene group, a substituted or unsubstituted arylsilylene group having 6 to 30 ring-forming atoms, O, and S.

In some embodiments, in Formula 1A, $A_1$ and $A_2$ may each independently be selected from a single bond, $C(R_x)(R_y)$, $[C(R_x)(R_y)]_2$, $Si(R_x)(R_y)$, O, and S, provided that at least one selected from $A_1$ and $A_2$ may be selected from $C(R_x)(R_y)$, $[C(R_x)(R_y)]_2$, $Si(R_x)(R_y)$, O, and S, wherein $R_x$ and $R_y$ may each independently be selected from hydrogen, a $C_1$-$C_{10}$ alkyl group, an aryl group having 6 to 30 ring-forming atoms, and a heteroarylene group having 5 to 30 ring-forming atoms, but embodiments are not limited thereto.

In Formula 1A, $A_3$ may be selected from a substituted or unsubstituted $C_1$-$C_{10}$ trivalent alkyl group, a substituted or unsubstituted trivalent aryl group having 6 to 30 ring-forming atoms, and a substituted or unsubstituted trivalent heteroaryl group having 5 to 30 ring-forming atoms.

In some embodiments, in Formula 1A, $A_3$ may be selected from trivalent aryl groups having 6 to 30 ring-forming atoms, but embodiments are not limited thereto.

In Formula 1A, $A_4$ and $A_5$ may each independently be selected from a substituted or unsubstituted $C_1$-$C_{10}$ alkylene group, a substituted or unsubstituted aryl group having 6 to 30 ring-forming atoms, and a substituted or unsubstituted heteroarylene group having 5 to 30 ring-forming atoms, $A_4$ and $A_5$ may optionally be bound via a single bond, O, S, a substituted or unsubstituted $C_1$-$C_{10}$ alkylsilylene group, a substituted or unsubstituted arylsilylene group having 6 to 30 ring-forming atoms, or a crosslinking group.

In some embodiments, in Formula 1A, $A_4$ and $A_5$ may each independently be selected from a trivalent aryl group having 6 to 30 ring-forming atoms, and $A_4$ and $A_5$ may optionally be bound via a single bond, O, S, a substituted or unsubstituted $C_1$-$C_{10}$ alkylsilylene group, a substituted or unsubstituted arylsilylene group having 6 to 30 ring-forming atoms, or a crosslinking group, but embodiments are not limited thereto.

In some embodiments, in Formula 1, $Ar_1$ may be represented by Formula 1A-1, but embodiments are not limited thereto:

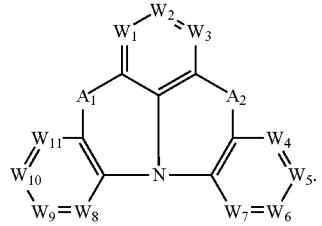

Formula 1A-1

In Formula 1A-1, $A_1$ and $A_2$ may be the same as $A_1$ and $A_2$ described in connection with Formula 1A, respectively, In Formula 1A-1, $W_1$ to $W_{11}$ may each independently be selected from a nitrogen atom and $CR_{11}$, wherein $R_{11}$ may be selected from a binding site to $L_1$, hydrogen, a deuterium atom, a substituted or unsubstituted $C_1$-$C_{10}$ alkyl group, a substituted or unsubstituted aryl group having 6 to 30 ring-forming atoms, and a substituted or unsubstituted heteroaryl group having 5 to 30 ring-forming atoms, $R_{11}$ may optionally be bound to two adjacent groups $R_{11}$ to form a condensed ring, $W_7$ and $W_8$ may optionally be bound via a single bond, O, and S, and at least one selected from $W_1$ to $W_{11}$ may have a C-($L_1$-binding site) structure.

In some embodiments, in Formula 1A-1, $W_1$ to $W_{11}$ may be $CR_{11}$, wherein $R_{11}$ may be selected from a binding site to $L_1$, hydrogen, a substituted or unsubstituted aryl group having 6 to 15 ring-forming carbon atoms, and a substituted or unsubstituted heteroaryl group having 5 to 15 ring-forming atoms, $R_{11}$ may optionally be bound to two adjacent groups $R_{11}$ to form a condensed ring, $W_7$ and $W_8$ may optionally be bound via a single bond, O, and S, and at least one selected from $W_1$ to $W_{11}$ may have a C-($L_1$-binding site) structure, but embodiments are not limited thereto.

In some embodiments, in Formula 1A-1, $R_{11}$ may be selected from a binding site to $L_1$, hydrogen, a phenyl group, a naphthyl group, a biphenyl group, a terphenyl group, a fluorenyl group, a pyrrolyl group, a pyridinyl group, a pyrazinyl group, a triazinyl group, a furanyl group, a benzofuranyl group, an isobenzofuranyl group, a quinolyl group, an isoquinolyl group, a quinoxalinyl group, a carbazolyl group, a furazanyl group, a thienyl group, a benzothienyl group, a dibenzofuranyl group, a dibenzothienyl group, and groups represented by Formula 1B, and $R_{11}$ may optionally be bound to two adjacent groups $R_{11}$ to form a benzene group, but embodiments are not limited thereto.

In some embodiments, in Formula 1A-1, at least one selected from $W_2$, $W_5$, and $W_{10}$ may have a C-($L_1$-binding site) structure, but embodiments are not limited thereto. When at least one selected from $W_2$, $W_5$, and $W_{10}$ has a C-($L_1$-binding site) structure, steric hindrance between groups represented by Formula 1 and groups represented by Formula 1B may be reduced, and thus, synthesis of the bicarbazole compound represented by Formula 1 may be efficient.

In some embodiments, in Formula 1, $Ar_1$ may be represented by one of Formulae 1-1 to 1-21, but embodiments are not limited thereto:

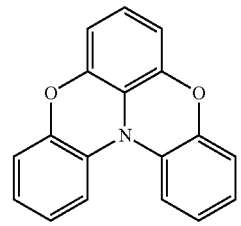

1-1

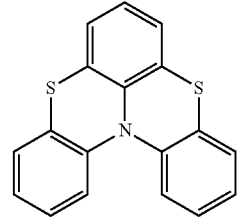

1-2

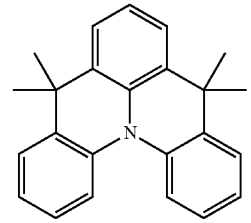

1-3

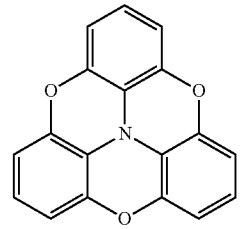

1-4

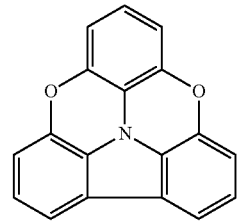

1-5

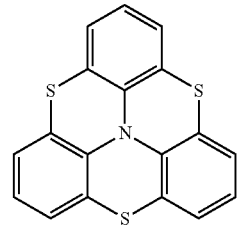

1-6

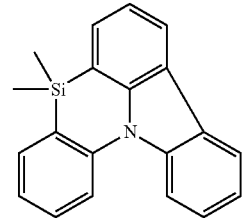

1-7

-continued
1-8
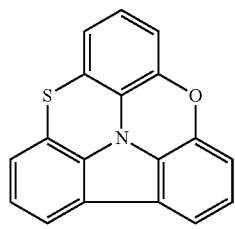
1-9
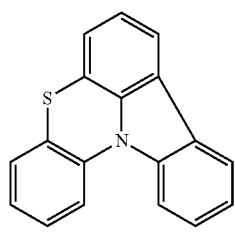
1-10
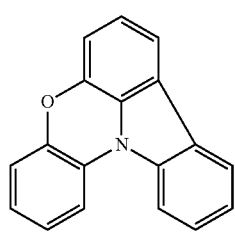
1-11
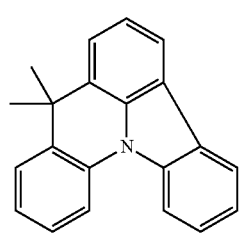
1-12
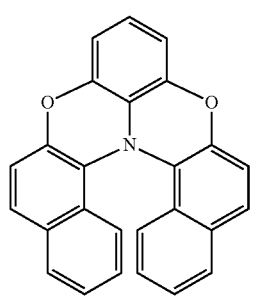
1-13
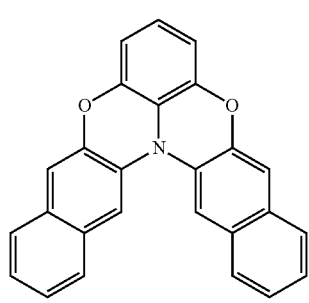
-continued
1-14
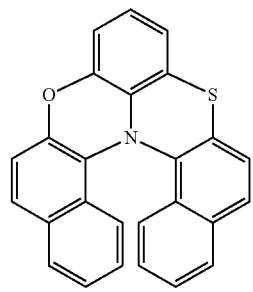
1-15
1-16
1-17
1-18
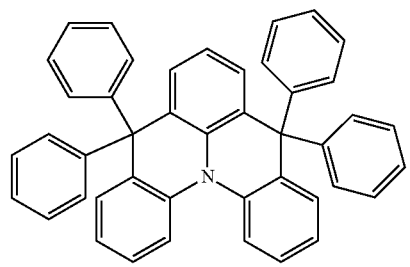

-continued

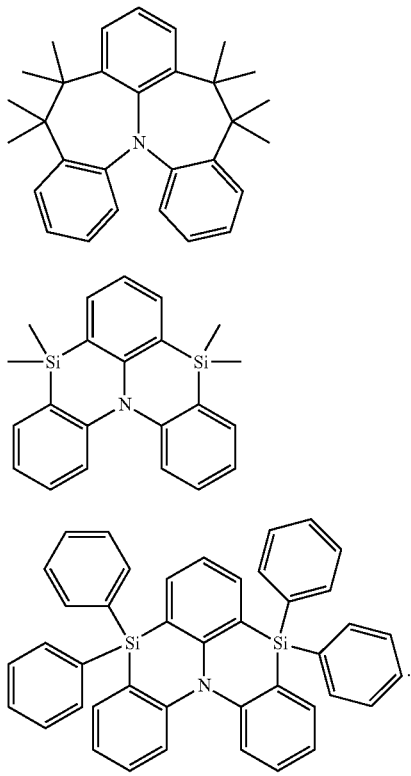

1-19

1-20

1-21

In Formulae 1-1 to 1-21, at least one hydrogen may be substituted with a group serving as a binding site to $L_1$.

In Formula 1, $Ar_2$ may be represented by Formula 1B:

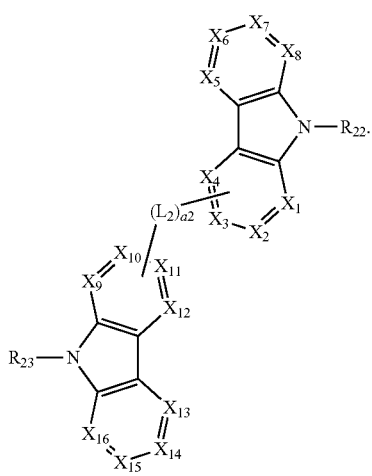

Formula 1B

In Formula 1B, $X_1$ to $X_{16}$ may each independently be selected from a nitrogen atom and $CR_{21}$, wherein $R_{21}$ may be selected from a binding site to $L_1$, a binding site to $L_2$, hydrogen, deuterium, a substituted or unsubstituted $C_1$-$C_{10}$ alkyl group, a substituted or unsubstituted aryl group having 6 to 30 ring-forming atoms, and a substituted or unsubstituted heteroaryl group having 5 to 30 ring-forming atoms, and $R_{21}$ may optionally be bound to adjacent $R_{21}$ to form a condensed ring.

In Formula 1B, two substituents of $X_1$ to $X_{16}$ may each have a C-($L_2$-binding site) structure.

In some embodiments, in Formula 1B, $X_1$ to $X_{16}$ may be $CR_{21}$, wherein $R_{21}$ may be selected from a binding site to $L_1$, a binding site to $L_2$, hydrogen, a substituted or unsubstituted aryl group having 6 to 30 ring-forming atoms, and a substituted or unsubstituted heteroaryl group having 5 to 30 ring-forming atoms, and at least two substituents of $X_1$ to $X_{16}$ may have a C-($L_2$-binding site) structure, but embodiments are not limited thereto.

In some embodiments, in Formula 1B, $R_{21}$ may be selected from a binding site to $L_1$, a binding site to $L_2$, hydrogen, a phenyl group, a naphthyl group, a biphenyl group, a terphenyl group, a fluorenyl group, a pyrrolyl group, a pyridinyl group, a pyrazinyl group, a triazinyl group, a furanyl group, a benzofuranyl group, an isobenzofuranyl group, a quinolyl group, an isoquinolyl group, a quinoxalinyl group, a carbazolyl group, a furazanyl group, a thienyl group, a benzothienyl group, a dibenzofuranyl group, a dibenzothienyl group, and groups represented by Formula 1A, but embodiments are not limited thereto.

In Formula 1B, $R_{22}$ and $R_{23}$ may each independently be selected from a binding site to $L_1$, a substituted or unsubstituted aryl group having 6 to 30 ring-forming atoms, and a substituted or unsubstituted heteroaryl group having 5 to 30 ring-forming atoms, and at least one selected from $R_{21}$ to $R_{23}$ may be a binding site to $L_1$.

In some embodiments, in Formula 1B, $R_{22}$ and $R_{23}$ may each independently be selected from a binding site to $L_1$, a phenyl group, a naphthyl group, an anthracenyl group, a phenanthrenyl group, a biphenyl group, a terphenyl group, a fluoranthenyl group, a fluorenyl group, a pyrrolyl group, a pyridinyl group, a pyrazinyl group, a triazinyl group, a furanyl group, a benzofuranyl group, an isobenzofuranyl group, a quinolyl group, an isoquinolyl group, a quinoxalinyl group, a carbazolyl group, a furazanyl group, a thienyl group, a benzothienyl group, a dibenzofuranyl group, a dibenzothienyl group, and groups represented by Formula 1A, but embodiments are not limited thereto.

In some embodiments, in Formula 1B, $X_3$ and $X_{11}$ may each have a C-($L_2$-binding site), but embodiments are not limited thereto.

In some embodiments, in Formula 1B, $X_3$ may have a C-($L_1$-binding site), $X_6$ may have a C-($L_1$-binding site), $X_{11}$ may have a C-($L_1$-binding site), $X_{14}$ may have a C-($L_1$-binding site), $R_{22}$ may be a binding site to $L_1$, or $R_{23}$ may be a binding site to $L_1$, but embodiments are not limited thereto. Here, steric hindrance between groups represented by Formula 1 and groups represented by Formula 1B may be reduced, and thus, synthesis of the bicarbazole compound represented by Formula 1 may be efficient.

In Formula 1, the subscript n1 denotes the number of repeating units of $Ar_1$, and may be an integer from 1 to 20. When n1 is 2 or greater, a plurality of $Ar_1$ may be identical to or different from each other.

In some embodiments, in Formula 1, n1 may be selected from 1, 2, 3, 4, and 5, but embodiments are not limited thereto. In some embodiments, in Formula 1, n1 may be selected from 1, 2, and 3, but embodiments are not limited thereto.

In Formula 1, the subscript n2 denotes the number of repeating units of $Ar_2$, and may be an integer from 1 to 20.

When n2 is 2 or greater, a plurality of $Ar_2$ may be identical to or different from each other.

In some embodiments, in Formula 1, n2 may be selected from 1, 2, 3, 4, and 5, but embodiments are not limited thereto. In some embodiments, in Formula 1, n2 may be selected from 1, 2, and 3, but embodiments are not limited thereto.

In Formula 1, when n1 and n2 are each independently an integer from 1 to 20, synthesis and handling of the bicarbazole compound represented by Formula 1 may be efficient.

In Formulae 1 and 1B, $L_1$ and $L_2$ may each independently be selected from a single bond and a substituted or unsubstituted arylene group having 6 to 30 ring-forming atoms.

In some embodiments, in Formulae 1 and 1B, $L_1$ and $L_2$ may each be a single bond, but embodiments are not limited thereto.

In Formula 1, the subscript a1 denote the number of repeating units of $L_1$, and may be selected from 0, 1, 2, and 3. When a1 is 2 or greater, a plurality of $L_1$ may be identical to or different from each other. When n1 is 0, $(L_1)_{a1}$ may be a single bond. In some embodiments, in Formula 1, a1 may be selected from 0 and 1, but embodiments are not limited thereto.

In Formula 1B, the subscript a2 denote the number of repeating units of $L_2$, and may be selected from 0, 1, 2, and 3. When a2 is 2 or greater, a plurality of $L_2$ may be identical to or different from each other. When n2 is 0, $(L_2)_{a2}$ may be a single bond. In some embodiments, in Formula 1B, a2 may be selected from 0 and 1, but embodiments are not limited thereto.

In some embodiments, the bicarbazole compound represented by Formula 1 may be selected from Compounds 1 to 58, but embodiments are not limited thereto:

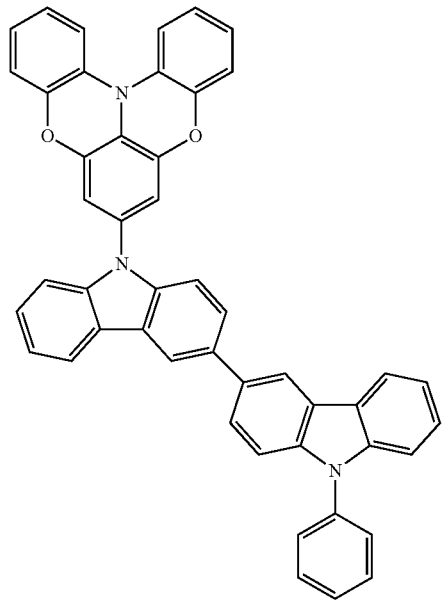

1

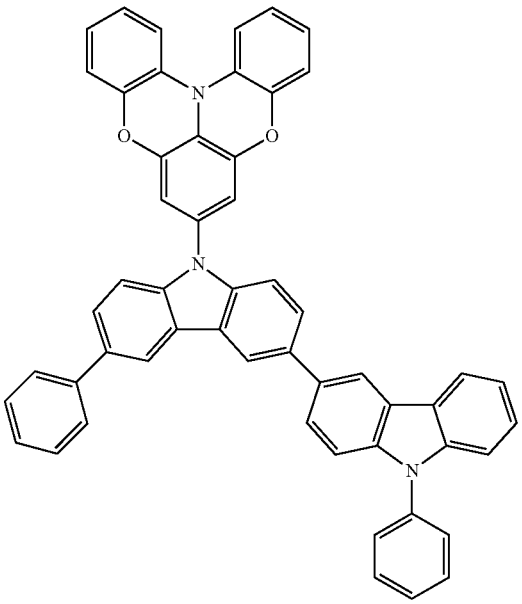

2

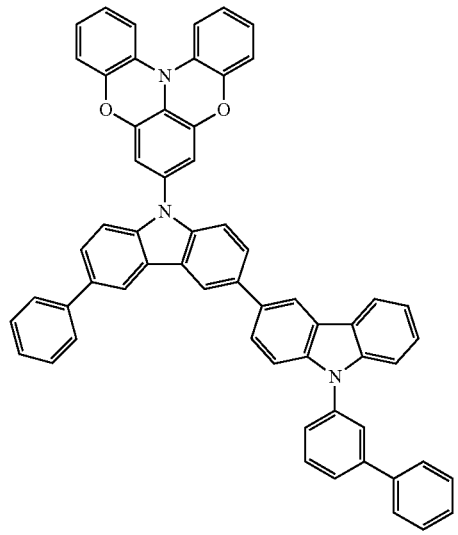

3

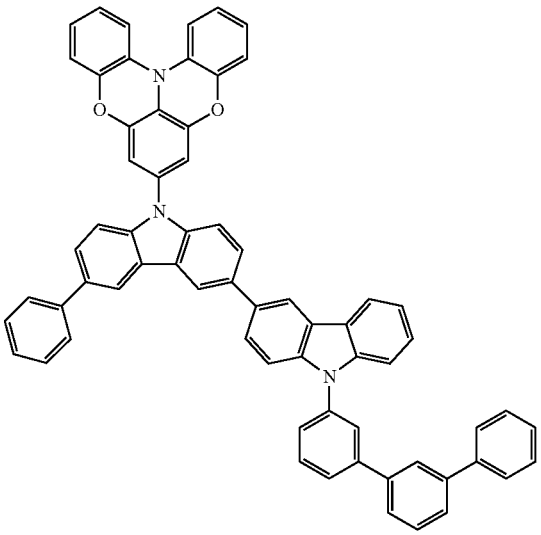

4

-continued
5
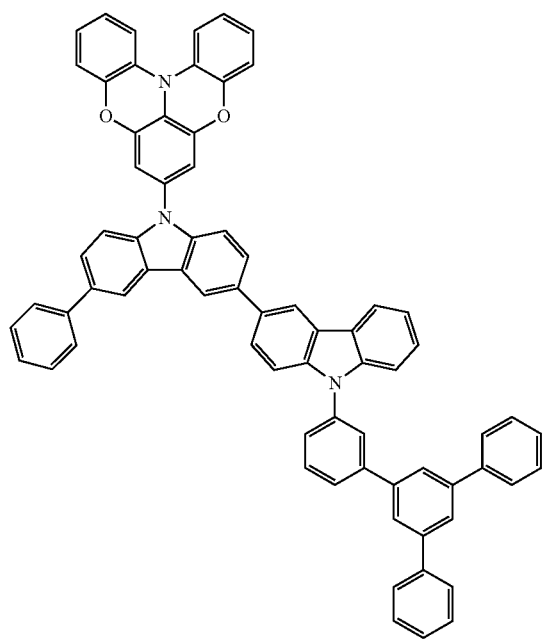
6
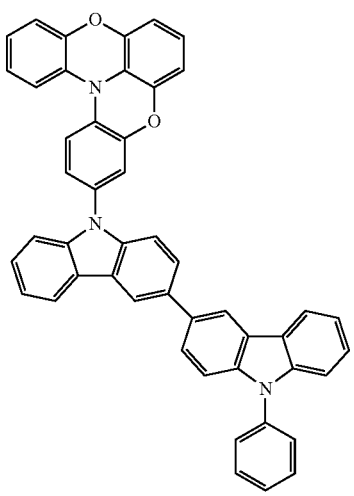
7
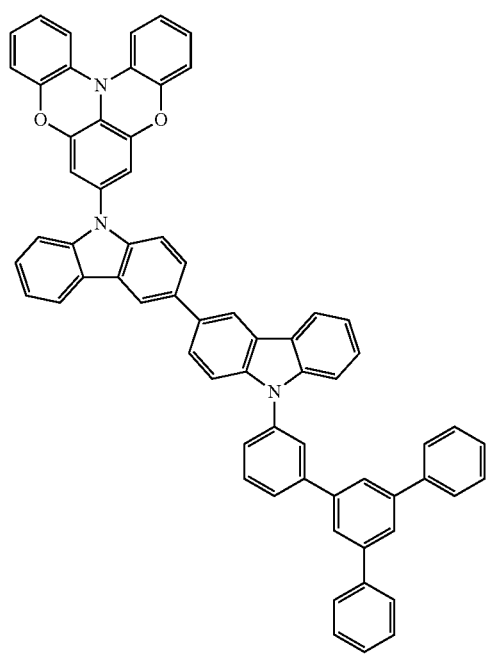
8
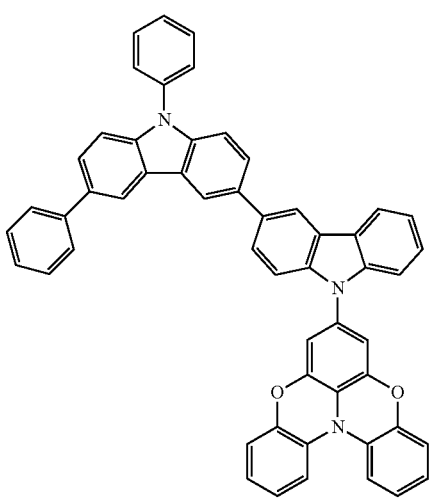

-continued
9
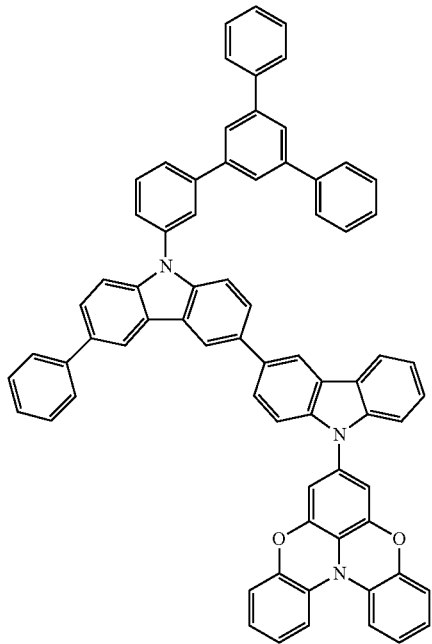
10
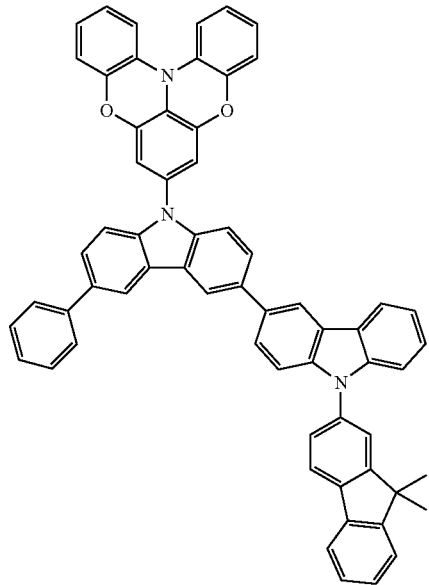
11
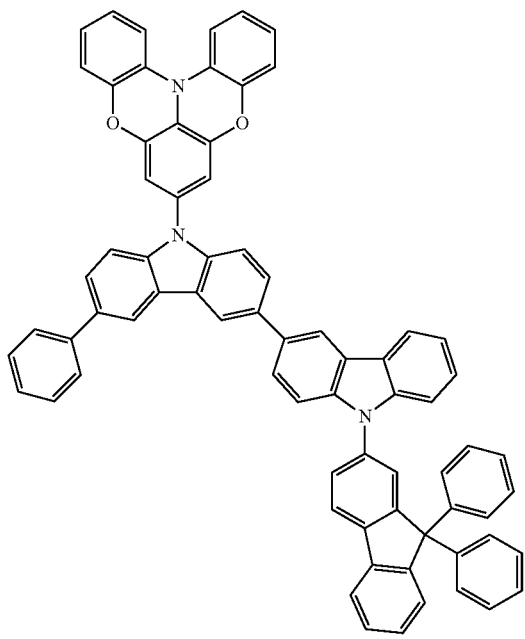
12
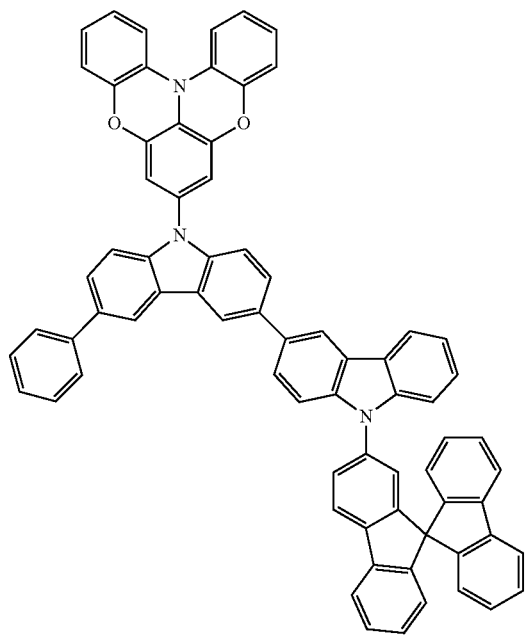

-continued
13
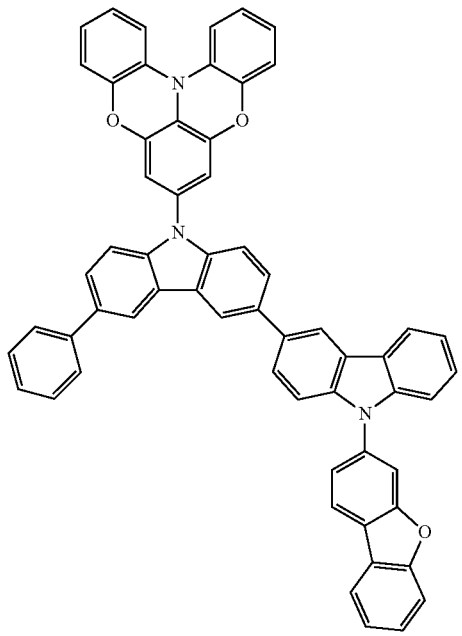
14
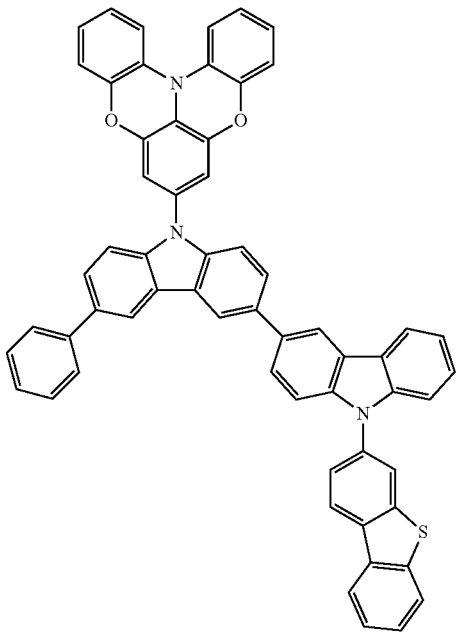
15
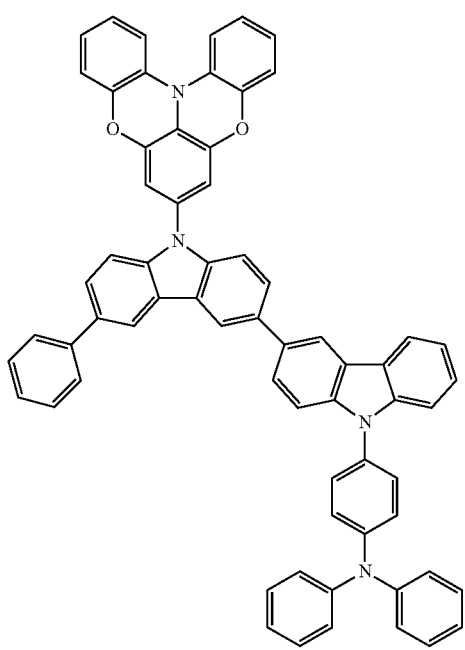
16
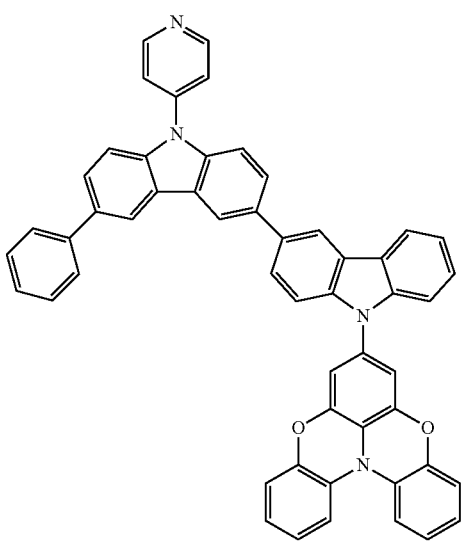

17
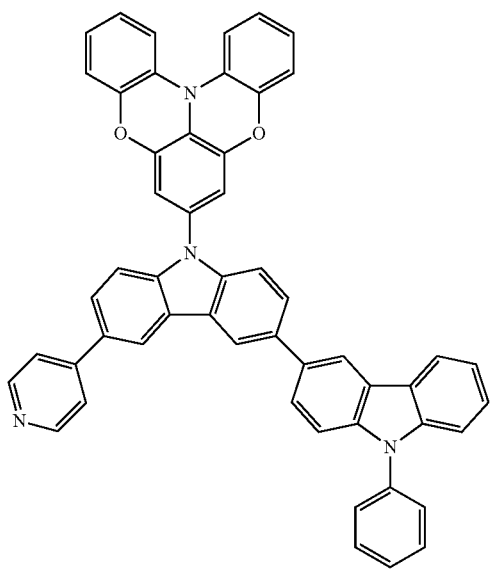
18
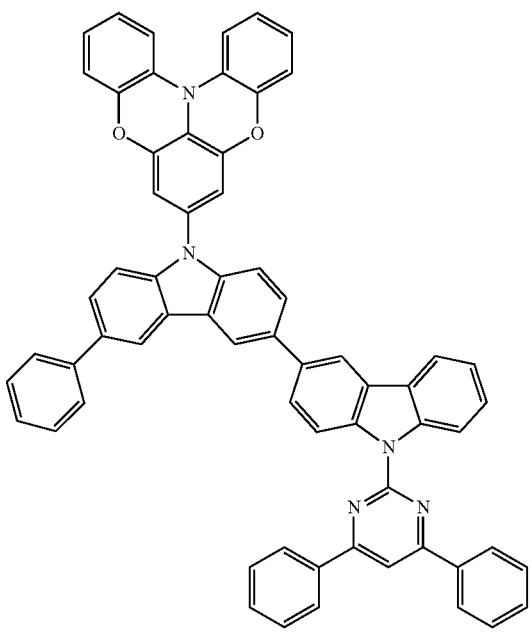
19
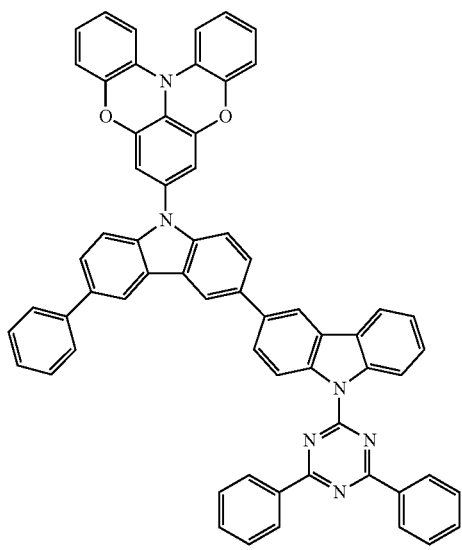
20
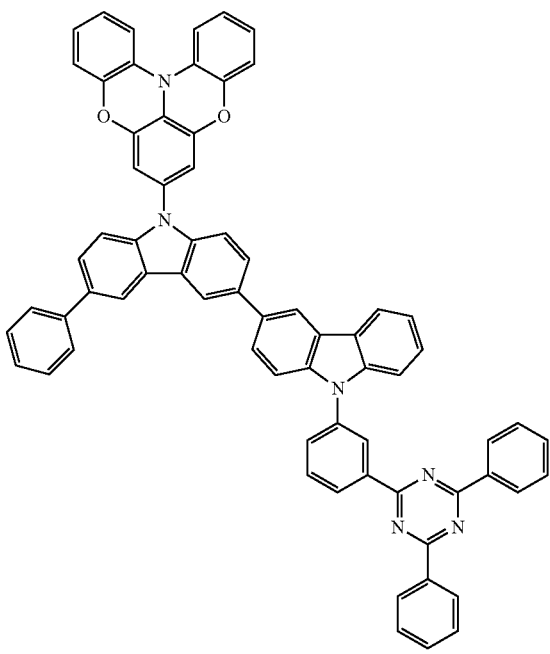

-continued
21
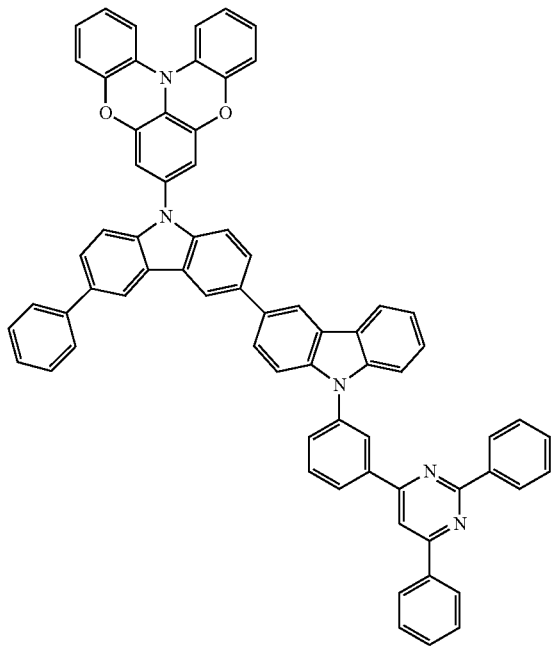
22
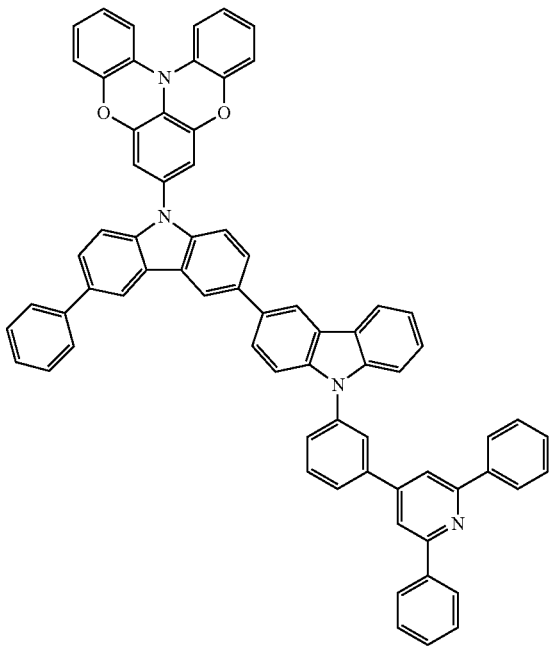
23
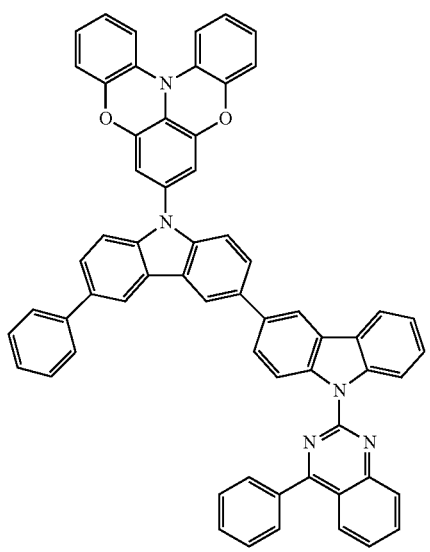
24
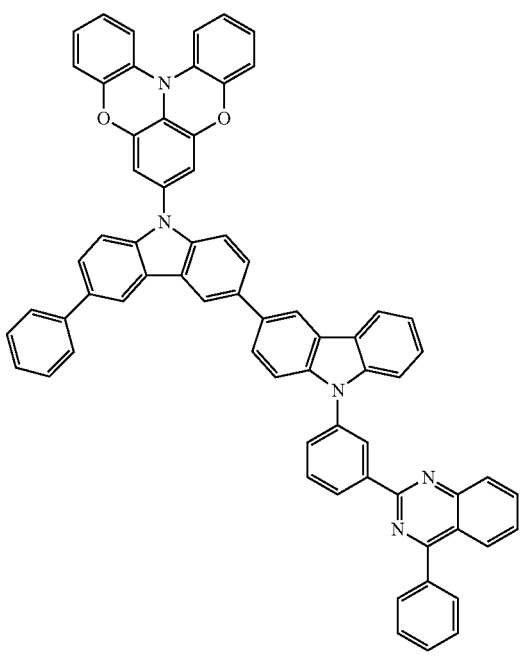

-continued
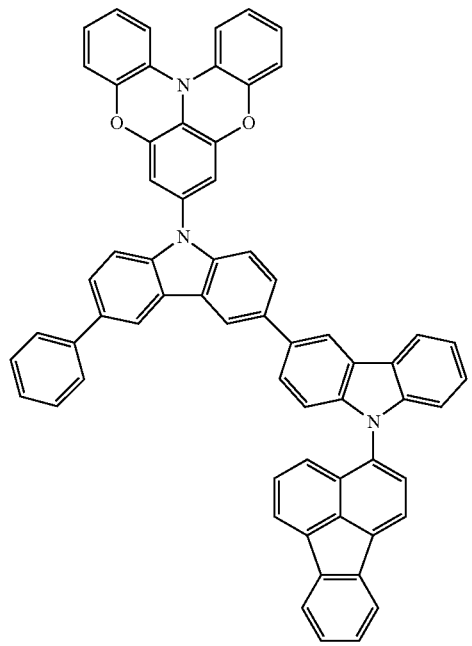
25
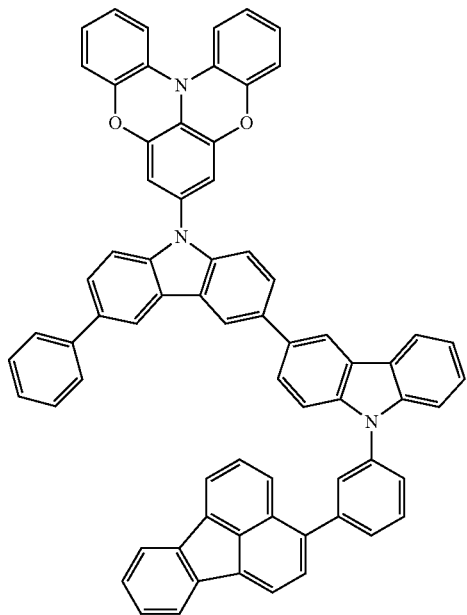
26
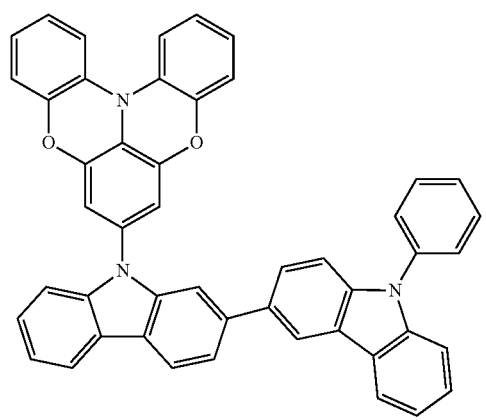
27
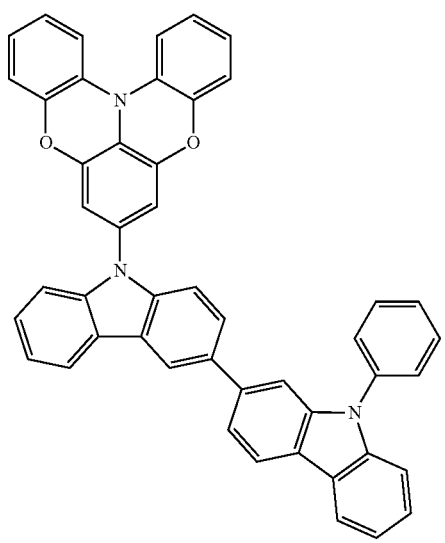
28

27
28
-continued
29 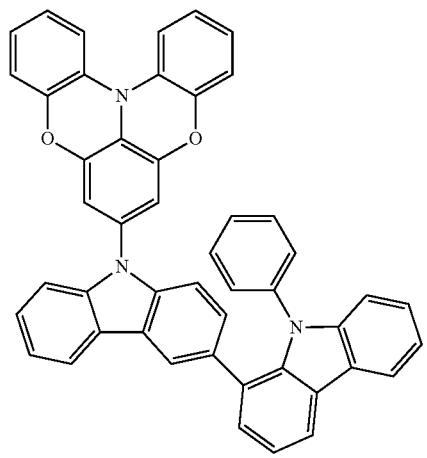
30 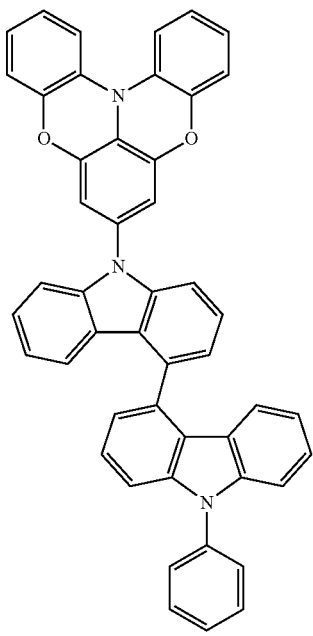
31 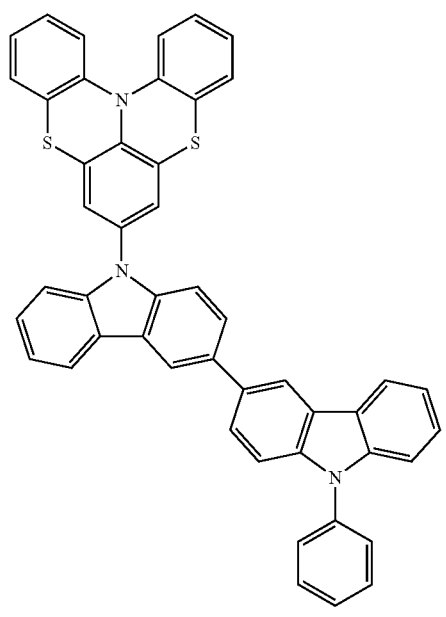
32 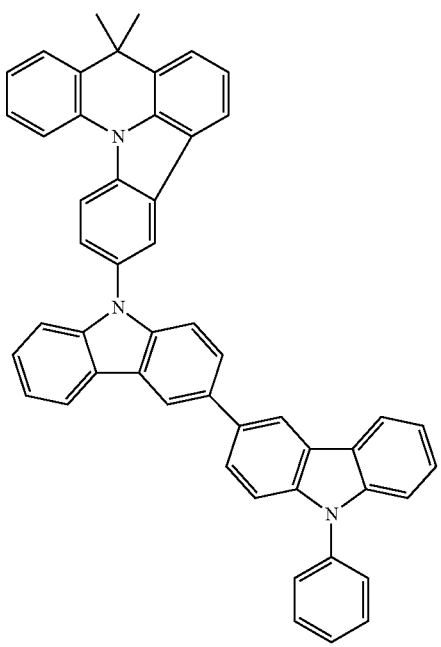

-continued
33
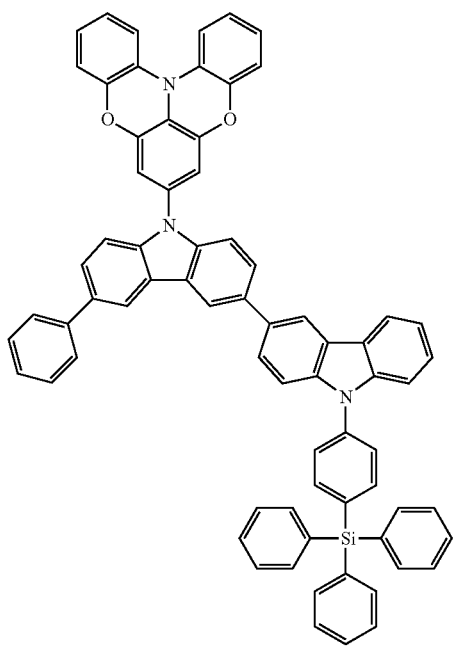
34
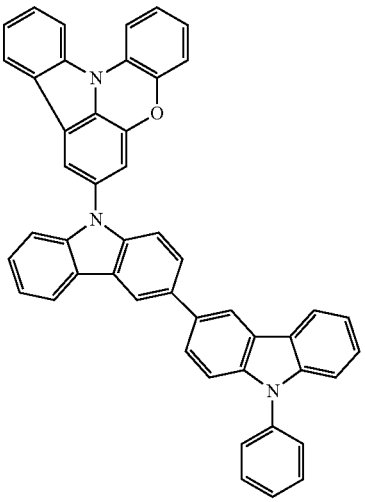
35
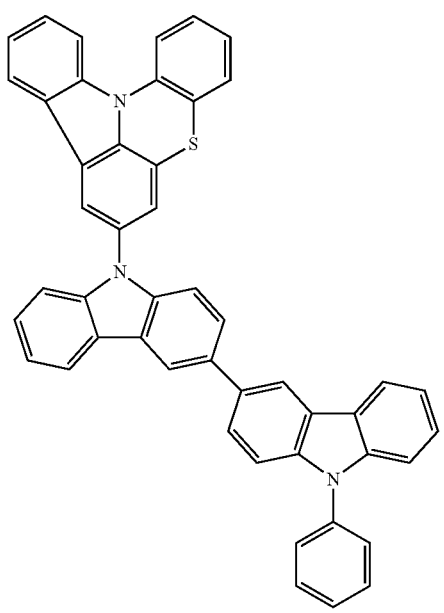
36
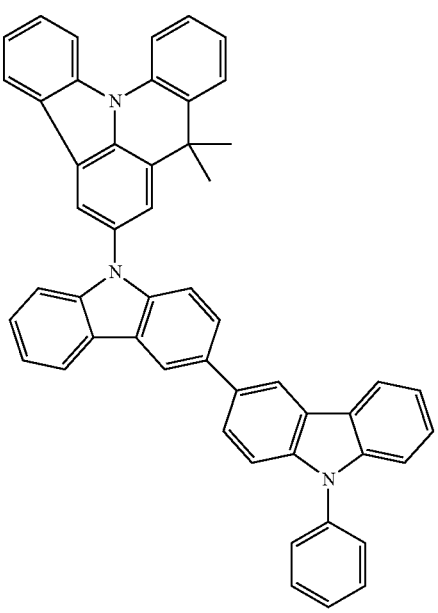

37
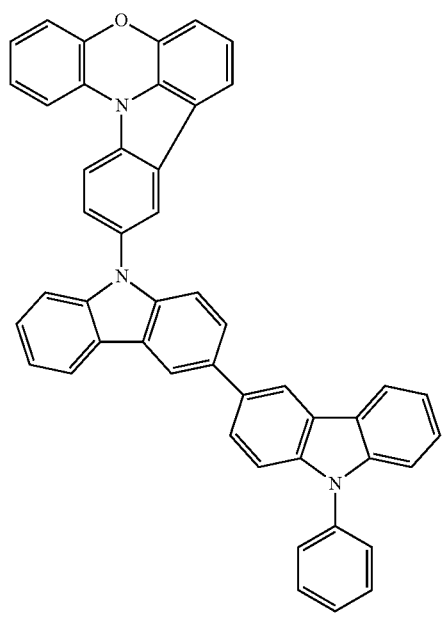
38
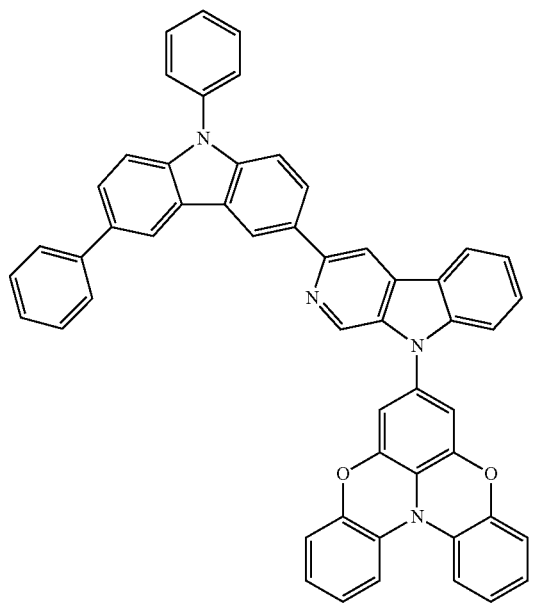
39
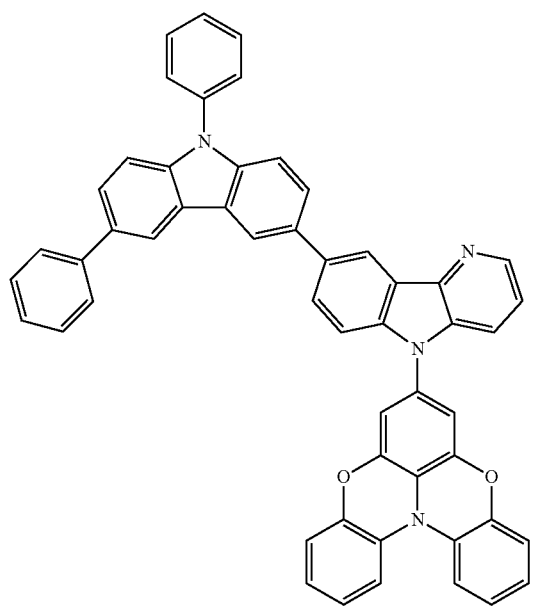
40
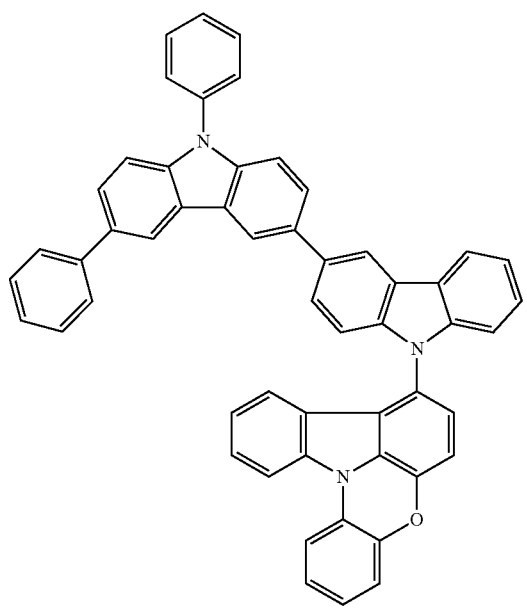

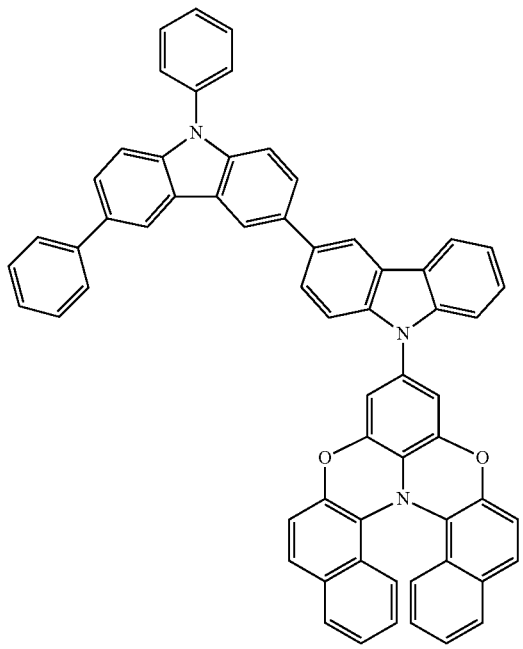
41
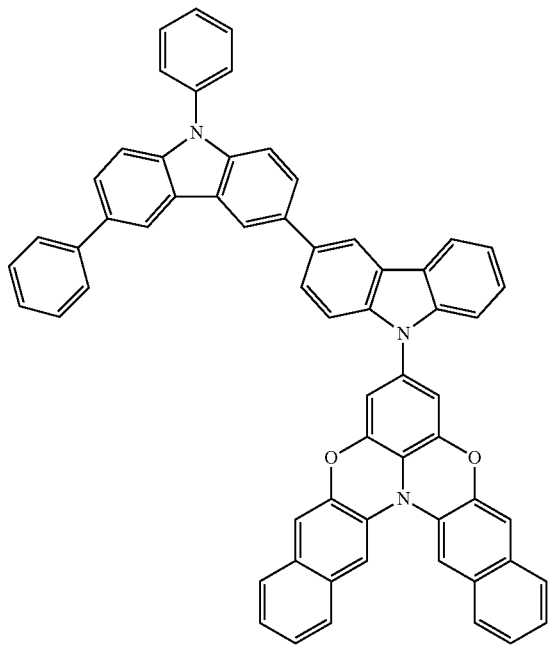
42
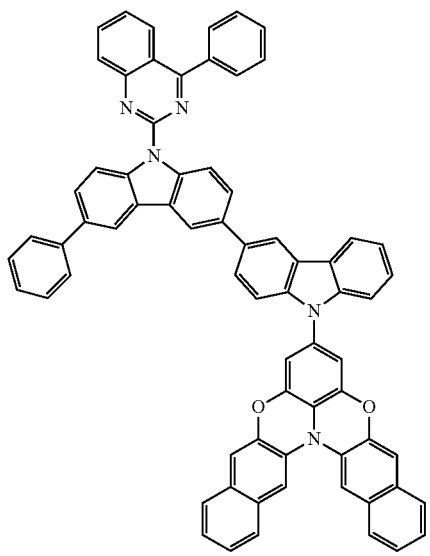
43
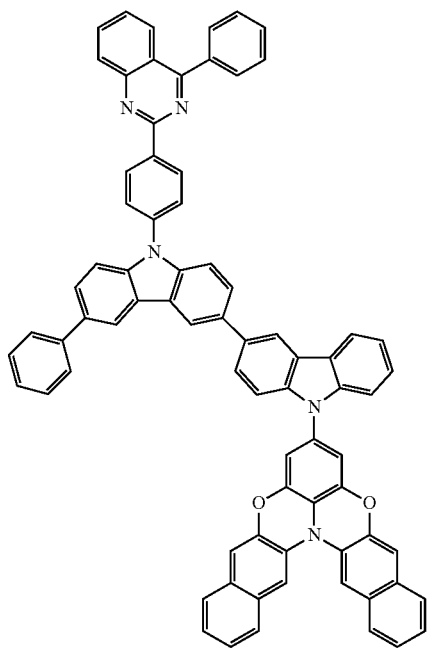
44

45
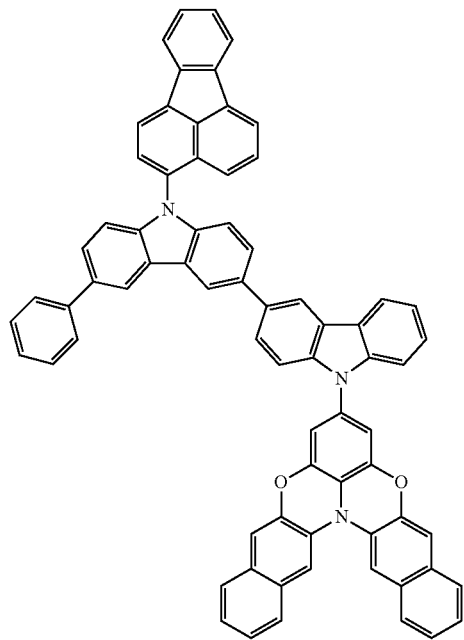
46
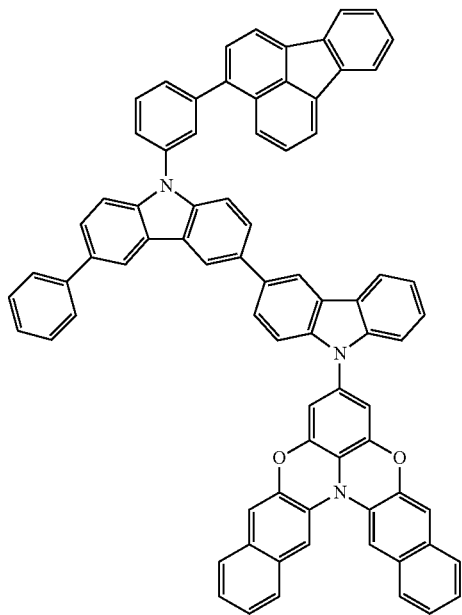
47
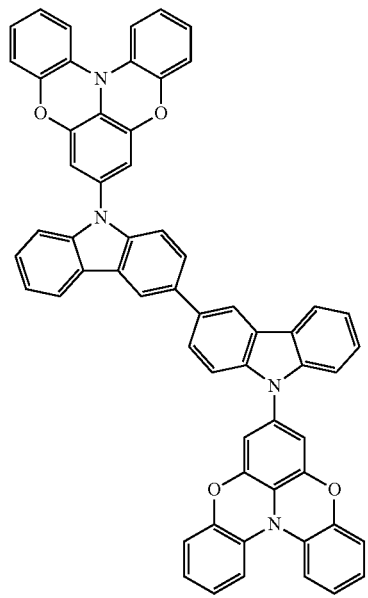
48
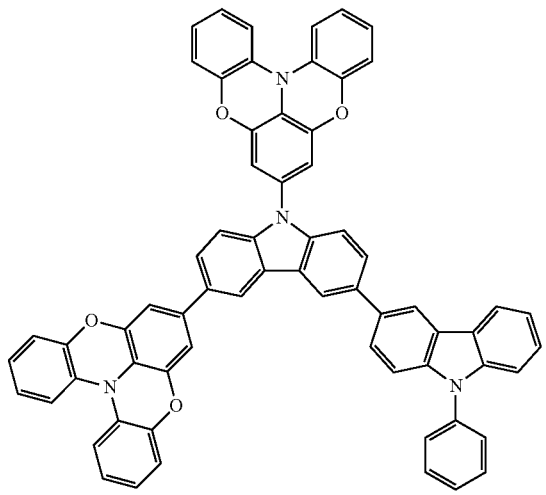

-continued
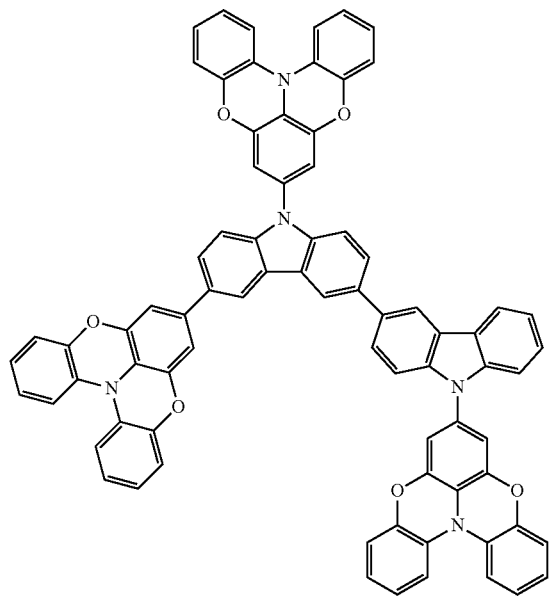
49
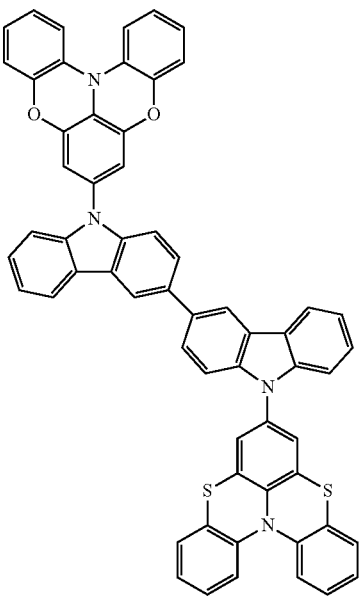
50
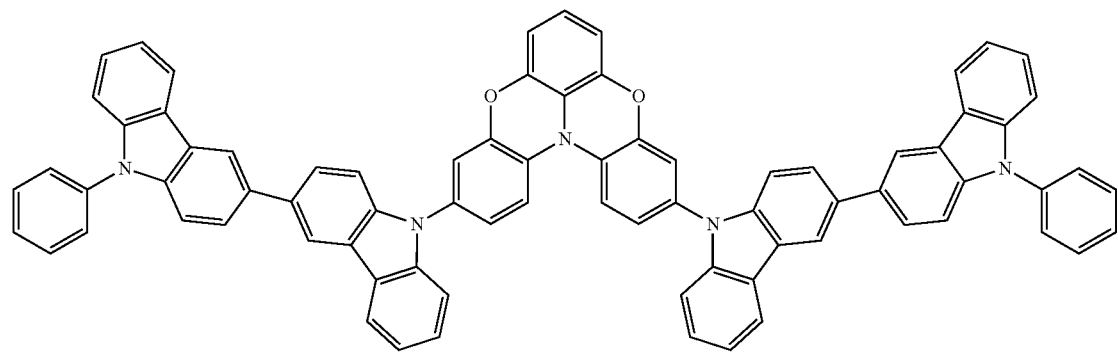
51

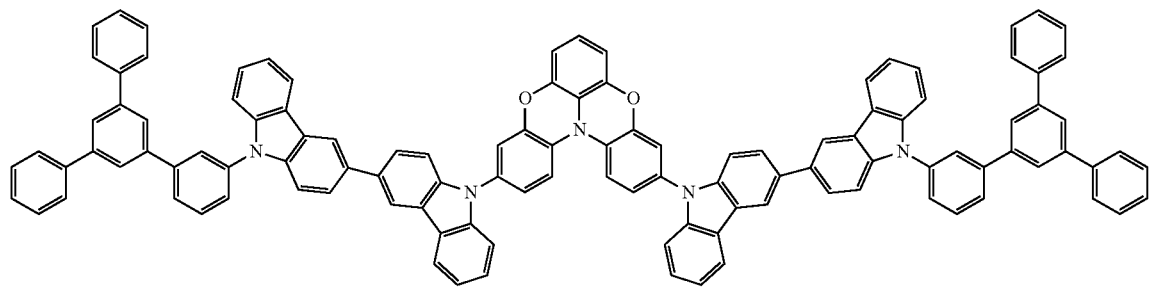
52
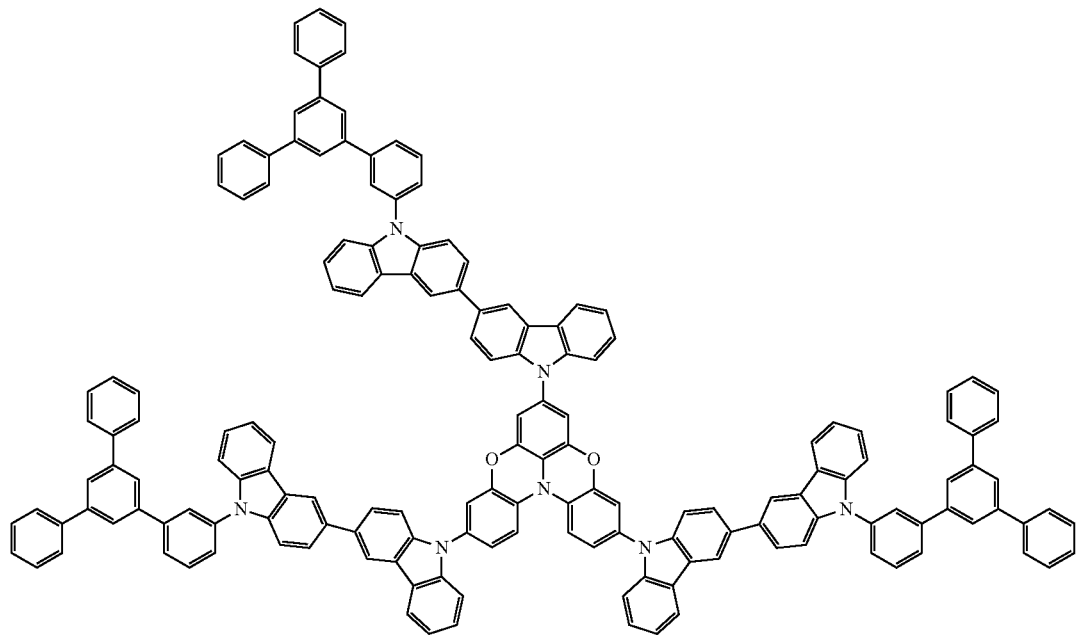
53

-continued
54
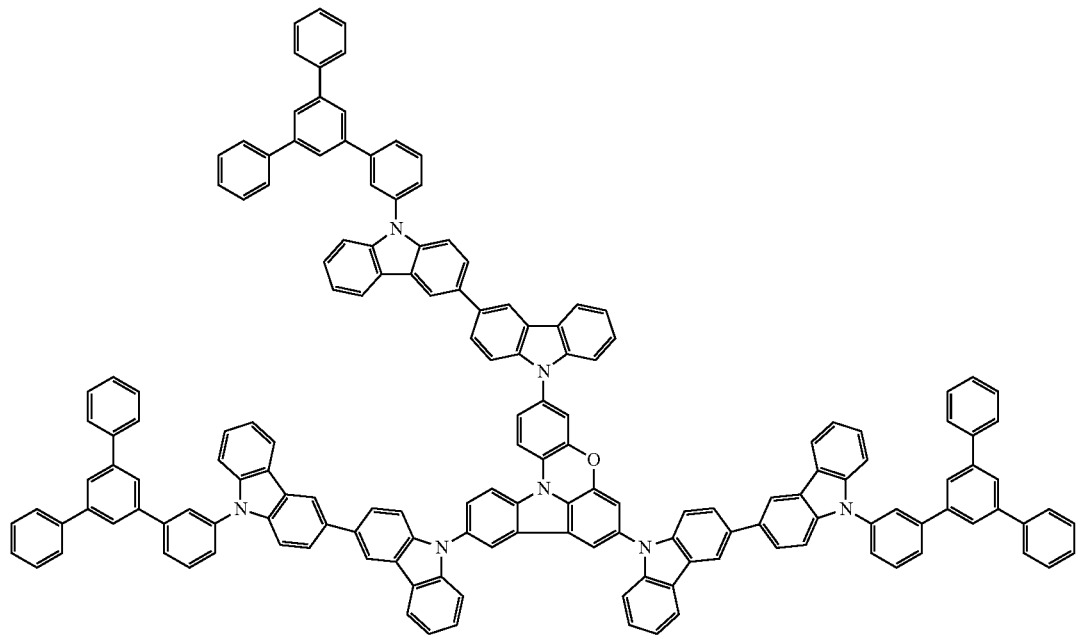
55
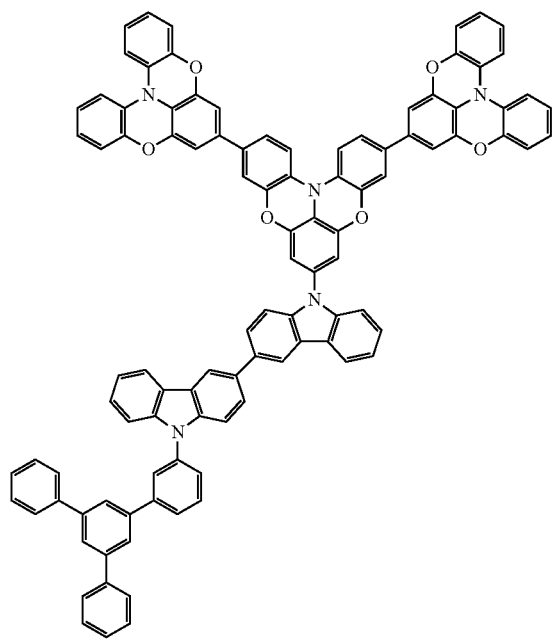

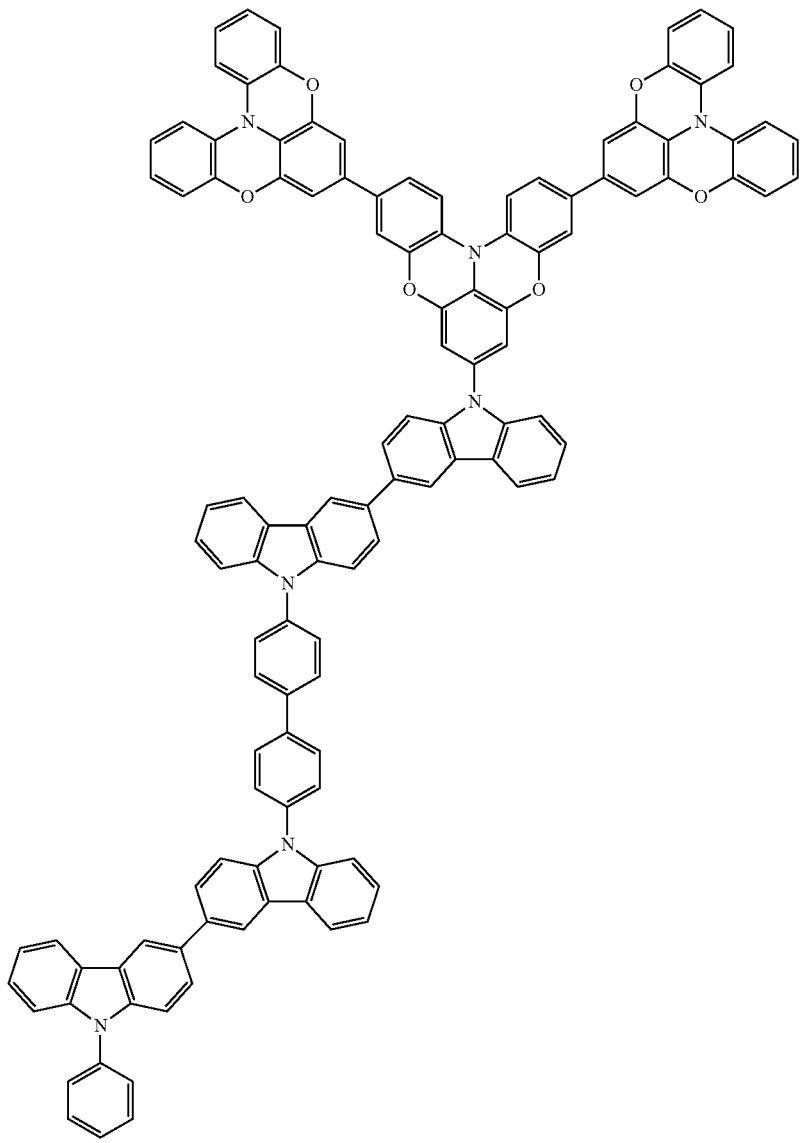
56

-continued

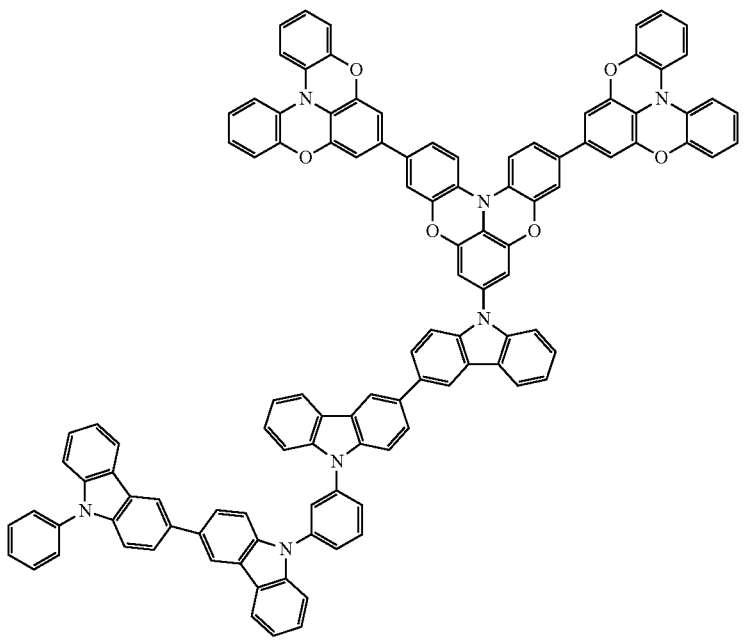

57

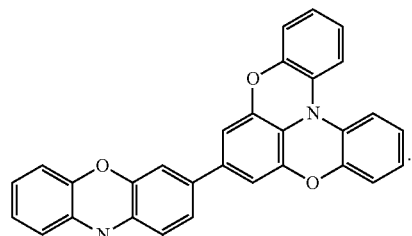

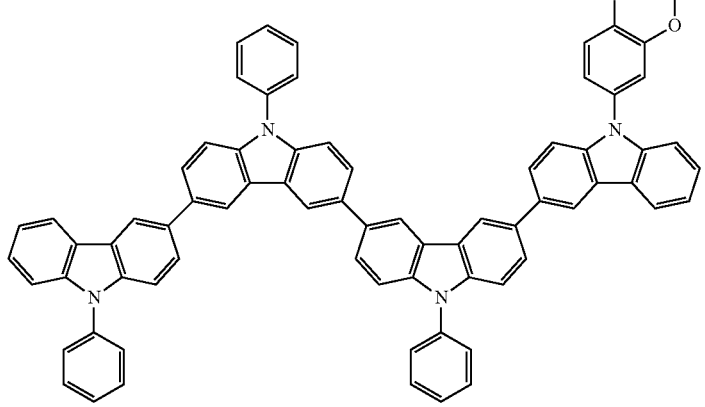

58

The bicarbazole compound represented by Formula 1 may include at least one selected from groups represented by Formula 1A and groups represented by Formula 1B. Thus, the highest occupied molecular orbital (HOMO) energy level of the bicarbazole compound represented by Formula 1 may decrease. When the bicarbazole compound represented by Formula 1 is included in an emission layer, a difference between the HOMO energy level of the emission layer and that of a hole transport layer may decrease. Accordingly, when the bicarbazole compound represented by Formula 1 is used as a hole transport host, efficiency of hole transporting from the hole transport layer to the emission layer may improve, and consequently an organic light-emitting device including the bicarbazole compound may have improved emission lifespan and luminous efficiency. In this case, the hole transport layer may include a compound including an amine group, but embodiments are not limited thereto.

The bicarbazole compound represented by Formula 1 may be included in an organic layer disposed between a pair of electrodes in an organic light-emitting device. In some embodiments, the bicarbazole compound represented by Formula 1 may be included in an emission layer and be suitable to serve as a hole transport host (HT-host).

The bicarbazole compound represented by Formula 1 may be well soluble in an organic solvent (e.g., toluene). Thus, the bicarbazole compound represented by Formula 1 may form a stable thin film by solution coating. Accordingly, in an organic light-emitting device including the bicarbazole compound represented by Formula 1, an organic layer including the bicarbazole compound represented by Formula 1 may be formed by solution coating. Therefore, the organic light-emitting device may have improved emission characteristics and stability.

For example, WO 2011/107186 and WO 2012/118164 disclose a nitrogen-containing heteroaromatic compound, and that the nitrogen-containing heteroaromatic compound can be used as a hole transport layer. Further, WO 2015/102118 discloses a compound including a hetero-condensed ring, and that the compound can be used as a host material for an emission layer, Meanwhile, in order to produce large area devices with a low cost, manufacture of organic light-emitting devices by solution coating in place of vacuum-deposition is considered. The solution coating may be more efficient than the vacuum-deposition in preparing organic light-emitting devices. As a result, when the solution coating is used, materials for an organic light-emitting device may be used efficiently, large area devices may be easily manufactured, and the use of a high-priced vacuum-deposition apparatus is not necessary.

However, the vacuum-deposition is only used for the organic light-emitting devices including the compounds disclosed in WO 2011/107186, WO 2012/118164, and WO 2015/102118. That is, the solution coating is not suitable for the compounds disclosed in WO 2011/107186 and WO 2012/118164.

The inventive concept of the present disclosure is to resolve this problem. That is, the inventive concept is to provide a novel bicarbazole compound having improved emission lifespan and luminous efficiency, a material for an organic light-emitting device including the bicarbazole compound, and an organic light-emitting device including the material.

The bicarbazole compound represented by Formula 1 may be synthesized by a suitable known organic synthetic method. Methods of synthesizing the bicarbazole compound represented by Formula 1 should be readily apparent to those of ordinary skill in the art by referring to Examples described herein.

Organic Light-Emitting Device

Hereinafter, with reference to the FIGURE, an embodiment of an organic light-emitting device will be described in detail. The FIGURE is a schematic view of an organic light-emitting device according to an embodiment.

An organic light-emitting device 100 according to an example embodiment may include a substrate 110, a first electrode 120 disposed on the substrate 110, a hole injection layer 130 disposed on the first electrode 120, a hole transport layer 140 disposed on the hole injection layer 130, an emission layer 150 disposed on the hole transport layer 140, an electron transport layer 160 disposed on the emission layer 150, an electron injection layer 170 disposed on the electron transport layer 160, and a second electrode 180 disposed on the electron injection layer 170.

In the organic light-emitting device 100, the bicarbazole compound represented by Formula 1 may be, for example, included in at least one organic layer (e.g., at least one organic layer selected from the hole injection layer 130, the hole transport layer 140, the emission layer 150, the electron transport layer 160, and the electron injection layer 170 disposed between the first electrode 120 and the second electrode 180. In some embodiments, the bicarbazole compound represented by Formula 1 may be included in the emission layer 150 as a hole transport host. In some embodiments, the bicarbazole compound represented by Formula 1 may be included in an organic layer other than the emission layer 150. For example, the bicarbazole compound represented by Formula 1 may be included in the hole injection layer 130 and/or the hole transport layer as a hole transport material.

An organic layer including the bicarbazole compound represented by Formula 1 may be formed by, for example, solution coating. In some embodiments, the organic layer including the bicarbazole compound represented by Formula 1 may be formed by solution coating, such as spin coating, casting, micro-gravure coating, gravure coating, bar coating, roll coating, wire bar coating, dip coating, spray coating, screen printing, flexographic printing, offset printing, or ink-jet printing.

In solution coating, a material for an organic light-emitting device including the bicarbazole compound represented by Formula 1 may be coated to form an organic layer. In this case, the material for an organic light-emitting device may include a solvent. Examples of the material for an organic light-emitting device including the solvent include an ink composition used in ink-jet printing and a film-forming composition used in spin coating, but embodiments are not limited thereto. The solvent included in the material for an organic light-emitting device may be any suitable solvent that may dissolve the bicarbazole compound represented by Formula 1. For example, the solvent may include toluene, but embodiments are not limited thereto.

The organic layer including the bicarbazole compound represented by Formula 1 may also be, depending on a molecular weight of the bicarbazole compound, formed by vacuum-deposition. Methods of forming an organic layer of the organic light-emitting device 100 according to one or more embodiments are not particularly limited. For example, vacuum-deposition or solution coating may be used in forming an organic layer thereof.

The substrate 110 may be any suitable substrate generally used in organic light-emitting devices. For example, the substrate 110 may be a glass substrate, a silicon substrate, or a transparent plastic substrate, but embodiments are not limited thereto.

The first electrode 120 may be formed on the substrate 110. The first electrode 120 may be an anode, and be formed of a material with a high work function selected from a metal, an alloy, or a conductive compound. For example, the first electrode 120 may be a transparent electrode including indium tin oxide ($In_2O_3$—$SnO_2$, ITO), indium zinc oxide ($In_2O_3$—ZnO), tin oxide ($SnO_2$), or zinc oxide (ZnO), each having excellent transparency and conductivity. The first electrode 120 may be a reflective electrode that may be formed by stacking magnesium (Mg) or aluminum (Al) on the transparent electrode.

The hole injection layer 130 may be formed on the first electrode 120. The hole injection layer 130 may facilitate hole injection from the first electrode 120. In some embodiments, the hole injection layer 130 may be formed to a thickness in a range of about 10 nanometers (nm) to about 1,000 nm, and in some embodiments, about 10 nm to about 100 nm.

The hole injection layer 130 may include a known hole injection material. Examples of the known hole injection material forming the hole injection layer 130 include poly (ether ketone)-containing triphenylamine (TPAPEK), 4-isopropyl-4'-methyl diphenyl iodonium tetrakis (pentafluorophenyl) borate (PPBI), N,N'-diphenyl-N,N'-bis-[4-(phenyl-m-tolyl-amino)-phenyl]-biphenyl-4,4'-diamine (DNTPD), copper phthalocyanine, 4,4',4''-tris(3-methyl phenyl amino)

triphenylamine (m-MTDATA), N,N'-di(1-naphthyl)-N,N'-diphenylbenzidine (NPB), 4,4',4"-tris (diphenyl amino) triphenylamine (TDATA), 4,4',4"-tris(N,N-2-naphthyl phenyl amino) triphenylamine (2-TNATA), polyaniline/dodecylbenzene sulfonic acid (PANI/DBSA), poly(3,4-ethylenedioxythiophene)/poly(4-styrene sulfonate (PEDOT/PSS), polyaniline/10-camphor sulfonic acid (PANI/CSA), and polyaniline/poly(4-styrene sulfonate (PANI/PSS).

The hole transport layer 140 may be formed on be hole injection layer 130. The hole transport layer 140 may facilitate hole transport. In some embodiments, the hole transport layer 140 may be formed to a thickness in a range of about 10 nm to about 150 nm. The hole transport layer 140 may include the bicarbazole compound represented by Formula 1.

The hole transport layer 140 may include a known hole transport material. Examples of the known hole transport material include carbazole derivatives, e.g., 1,1-bis[(di-4-tolylamino)phenyl] cyclohexane (TAPC), N-phenylcarbazole, and polyvinylcarbazole, N,N'-bis(3-methylphenyl)-N,N'-diphenyl-[1,1-biphenyl]-4,4'-diamine (TPD), 4,4',4"-tris (N-carbazolyl) triphenylamine (TCTA), N,N'-di(1-naphthyl)-N,N'-diphenylbenzidine (NPB), and poly(9,9-dioctyl-fluorene-co-N-(4-butylphenyl)-diphenylamine (TFB).

The emission layer 150 may be formed on the hole transport layer 140. The emission layer 150 emit light by fluorescence or phosphorescence. The emission layer 150 may include the bicarbazole compound represented by Formula 1. The emission layer 150 may include a known electron transport host (ET-host) material and a known dopant material.

The emission layer 150 may be formed by solution coating, e.g., spin coating or ink-jet coating. The emission layer 150 may be, for example, formed to a thickness in a range of about 10 nm to about 60 nm, In the organic light-emitting device 100 according to an embodiment, a dopant material included in the emission layer 150 may be capable of emitting light from triplet excitons (i.e., emission by phosphorescence). In this case, the organic light-emitting device 100 may have improved emission lifespan.

In addition to the bicarbazole compound represented by Formula 1, Examples of a HT-host material or an ET-host material in the emission layer 150 include tris(8-quinolinato) aluminum ($Alq_3$), 4,4'-bis(carbazol-9-yl)biphenyl (CBP), poly(n-vinylcarbazole (PVK), 9,10-di(naphthalene-yl)anthracene (ADN), 4,4',4"-tris(N-carbazolyl)triphenylamine (TCTA), 1,3,5-tris(N-phenyl-benzimidazol-2-yl)benzene (TPBI) 3-tert-butyl-9,10-di(naphth-2-yl)anthracene (TBADN), distyrylarylene (DSA), and 4,4'-bis(9-carbazole)-2,2'-dimethyl-biphenyl (dmCBP).

In addition, the emission layer 150 may include, as a dopant material, perylene and a derivative thereof, rubrene and a derivative thereof, coumarin and a derivative thereof, 4-dicyanomethylene-2-(p-dimethylaminostyryl)-6-methyl-4H-pyran (DCM) and a derivative thereof, an iridium complex, e.g., bis[2-(4,6-difluorophenyl)pyridinate] picolinate iridium (III) (Flrpic), bis(1-phenylisoquinoline)(acetylacetonate) iridium (III) ($Ir(piq)_2(acac)$), and tris(2-phenylpyridine) iridium (III) ($Ir(ppy)_3$), an osmium complex, and a platinum complex.

The electron transport layer 160 may be formed on the emission layer 150. The electron transport layer 160 may serve to transport electrons, and may be formed by vacuum-deposition, spin coating, or ink-jet printing. The electron transport layer 160 may be, for example, formed to a thickness in a range of about 15 nm to about 50 nm.

The electron transport layer 160 may include a known electron transport material. Examples of the known electron transport material include tris(8-quinolinato) aluminum ($Alq_3$) and a compound including a nitrogen-containing aromatic ring. Examples of the compound including a nitrogen-containing aromatic ring include a compound including a pyridine ring such as 1,3,5-tri[(3-pyridyl)-phen-3-yl]benzene, a compound including a triazine ring such as 2,4,6-tris(3'-(pyridin-3-yl)biphenyl-3-yl)-1,3,5-triazine, and a compound including an imidazole ring such as 2-(4-(N-phenylbenzimidazolyl-1-yl-phenyl)-9,10-dinaphthylanthracene. In some embodiments, as an electron transport material, a commercially available item may also be used. Examples of the commercially available item include KLET-01, KLET-02, KLET-03, KLET-10, and KLET-M1 (available from Chemipro Kasei Corporation).

The electron injection layer 170 may be formed on the electron transport layer 160. The electron injection layer 170 may facilitate electron injection from the second electrode 180, and may be formed by vacuum-deposition. In some embodiments, the electron injection layer 170 may be formed to a thickness in a range about 0.3 nm to about 9 nm. The electron injection layer 170 may include a known electron injection material. For example, the electron injection layer 170 may be formed of a lithium compound, e.g., (8-hydroxyquinolinato)lithium (Liq) and lithium fluoride (LiF), sodium chloride (NaCl), cesium fluoride (CSF), lithium oxide ($Li_2O$), or barium oxide (BaO).

The second electrode 180 may be formed on the electron injection layer 170. The second electrode 180 may be a cathode, and may be formed of a material with a low work function selected from a metal, an alloy, and a conductive compound. For example, the second electrode 180 may be formed as a reflective electrode including a metal, e.g., lithium (Li), magnesium (Mg), aluminum (Al), or calcium (Ca), or an alloy, e.g., an aluminum-lithium (Al—Li) alloy, a magnesium-indium (Mg—In) alloy, or a magnesium-silver (Mg—Ag) alloy. In some embodiments, the second electrode 180 may be formed as a transparent electrode having a thickness of 20 nm or less and including a thin film of the metal or the alloy, or a transparent conductive film including indium tin oxide ($In_2O_3$—$SnO_2$) or indium zinc oxide ($In_2O_3$—ZnO).

Since the organic light-emitting device 100 according to an embodiment includes an organic layer including the bicarbazole compound represented by Formula 1, luminous efficiency and emission lifespan thereof may improve.

Furthermore, a stacking structure of the organic light-emitting device 100 according to an embodiment is not limited to the foregoing description. The organic light-emitting device 100 according to an embodiment may have a different stacking structure known in the art. For example, the organic light-emitting device 100 may not include at least one selected from the hole injection layer 130, the hole transport layer 140, the electron transport layer 160, and the electron injection layer 170, or may further include another layer. In some embodiments, each layer of the organic light-emitting device 100 may be formed as a single layer or as multiple layers.

For example, in order to prevent diffusion of excitons or holes to the electron transport layer 160, the organic light-emitting device 100 may further include a hole blocking layer between the hole transport layer 140 and the emission layer 150. The hole blocking layer may be formed using, for example, an oxadiazole derivative, a triazole derivative, or a phenanthroline derivative.

Hereinafter, with reference to Examples and Comparative Examples, the bicarbazole compound represented by Formula 1 and an organic light-emitting device including the bicarbazole compound will be further described. However, these Examples are for illustrative purposes only, and thus, the bicarbazole compound and the organic light-emitting device according to an embodiment is not limited to the following Examples,

EXAMPLES

Synthesis Example 1: Synthesis of Compound 8

Compound 8 was synthesized following Reaction Scheme 1:

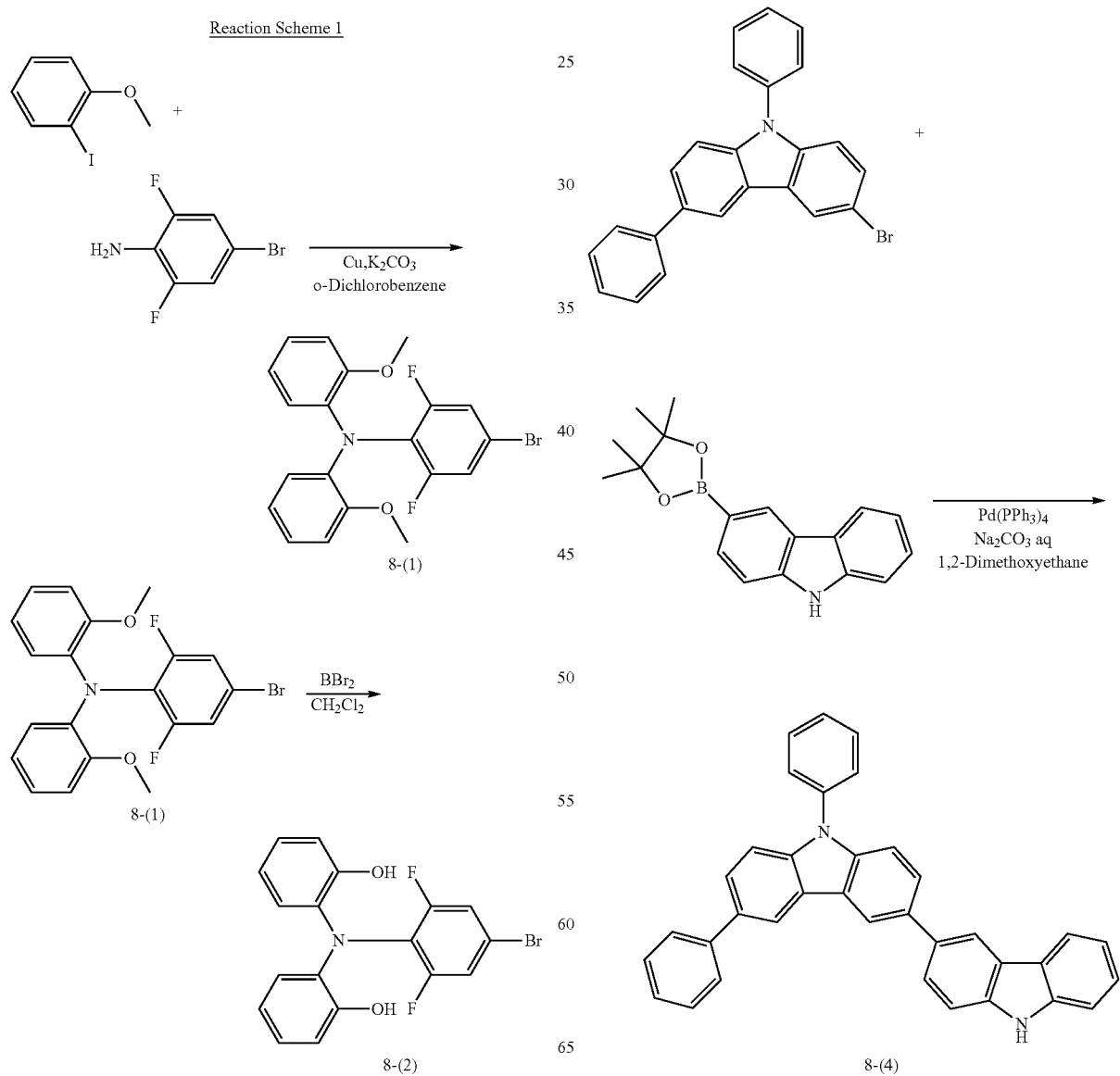

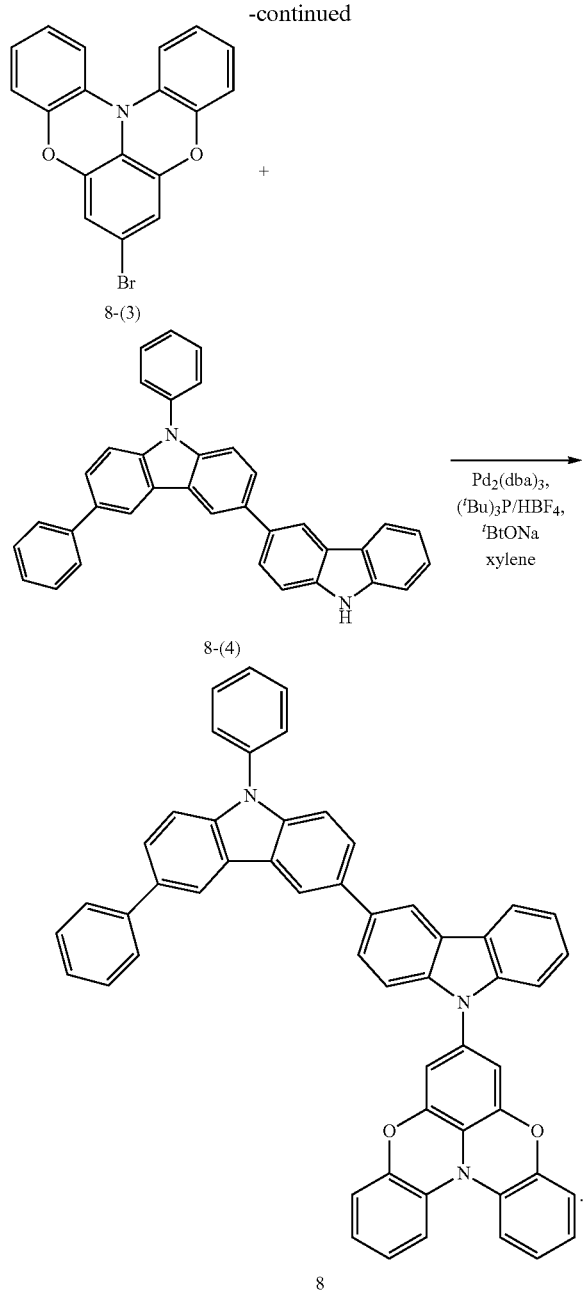

(1) Synthesis of Intermediate 8-(1)

40.0 grams (g) (192.3 millimoles, mmol) of 2-iodoanisole, 100.0 g (427.3 mmol) of 4-bromo-2,6-difluoroaniline, 111.0 g (803.2 mmol) of potassium carbonate ($K_2CO_3$), 15.6 g (246.0 mmol) of copper, and 520 milliliters (ml) of o-dichlorobenzene were added to a 2 liter (L) four-neck flask under argon, and the mixture was stirred at a temperature of 180° C. for 80 hours. Once the reaction was complete, the mixture was cooled to room temperature and the impurities were filtered by using a celite filter. A solvent was next removed from the filtrate, and the resultant was washed three times with 300 ml of hexane to obtain 48.0 g (114.2 mmol) of white powder Compound 8-(1) (yield: 26.7%).

(2) Synthesis of Intermediate 8-(2)

47.00 g (111.84 mmol) of Intermediate 8-(1) and 1,800 ml of anhydrous dichloromethane were added to a 3 L four-neck flask under argon, and the mixture was stirred at a temperature of −75° C. for 15 minutes. Subsequently, 230 ml of 1.0 molar (M) boron tribromide dichloromethane solution was added dropwise thereto. Then, the temperature of the mixture was raised to room temperature, and the mixture was stirred for 5 hours. Next, 1,000 ml of water was added to the reaction solution, and an organic layer was extracted therefrom using dichloromethane. The organic layer was concentrated and purified using column chromatography to obtain 38.0 g (96.9 mmol) of Intermediate 8-(2) (yield: 86.6%).

(3) Synthesis of Intermediate 8-(3)

37.00 g (94.35 mmol of Intermediate 8-(2), 39.00 g (283.00 mmol) potassium carbonate, 500 ml of dimethyl formamide were added to a 2 L four-neck flask under argon, and the mixture was stirred at a temperature of 110° C. for 10 hours. The mixture was cooled to room temperature, and 1,000 ml of water was added thereto to extract a white solid followed by filtration. The obtained solid was purified by recrystallization using a mixture solvent of chloroform and hexane to obtain 26.3 g (74.7 mmol) of Intermediate 8-(3) (yield: 79.1%).

(4) Synthesis of Intermediate 8-(4)

4.52 g (11.4 mmol) of 3-bromo-6,9-diphenylcarbazole, 3.50 g (11.9 mmol) of 3-(4,4,5,5-tetramethyl-1,3,2-dioxaborolan-2-yl)carbazole, 0.394 g (0.340 mmol) of tetrakis(triphenylphosphine)palladium, 30 ml of 1,2-dimethoxyethane, and 17 ml of 2 M sodium carbonate aqueous solution ($Na_2CO_3$ aqueous solution) were added to a 200 ml three-neck flask under argon, and the mixture was stirred at a temperature of 80° C. for 8 hours. The mixture was cooled to room temperature, and the impurities were filtered by using a celite filter. An organic layer obtained therefrom was concentrated and purified using column chromatography to obtain 2.06 g (4.25 mmol) of Intermediate 8-(4) (yield: 37.3%).

5) Synthesis of Compound 8

1.38 g (3.92 mmol) of Intermediate 8-(3), 2.00 g (4.13 mmol) of Intermediate 8-(4), 0.0760 g (0.0800 mmol) of tris(dibenzylideneacetone)dipalladium, 0.0960 g (0.330 mmol) of tetrafluoroboric acid tri-t-butylphosphine, 0.595 g (6.19 mmol) of sodium-t-butoxide, and 20 ml of dehydrated xylene were added to a 100 ml three-neck flask under argon, and the mixture was stirred at a temperature of 120° C. for 4 hours. The mixture was cooled to room temperature, and the impurities were filtered by using a celite filter. An organic layer obtained therefrom was concentrated and purified using column chromatography to obtain 2.27 g of Compound 8 (yield: 76.5%). The structure of Compound 8 was identified using liquid chromatography-mass spectrometry (LC-MS). It was found that the molecular weight (m/z value) of Compound 8 measured by LC-MS was 756 (M+H$^+$), equal to the calculated molecular weight of Compound 8 ($C_{54}H_{33}N_3O_2$), 756.

Synthesis Example 2: Synthesis of Compound 40

Compound 40 was synthesized in substantially the same manner as in Synthesis of Compound 8, except that the starting materials were appropriately changed. The structure of Compound 40 was identified using LC-MS. It was found that the molecular weight (m/z value) of Compound 40 measured by LC-MS was 740 (M+H$^+$), equal to the calculated molecular weight of Compound 40 ($C_{54}H_{33}N_3O_2$), 740.

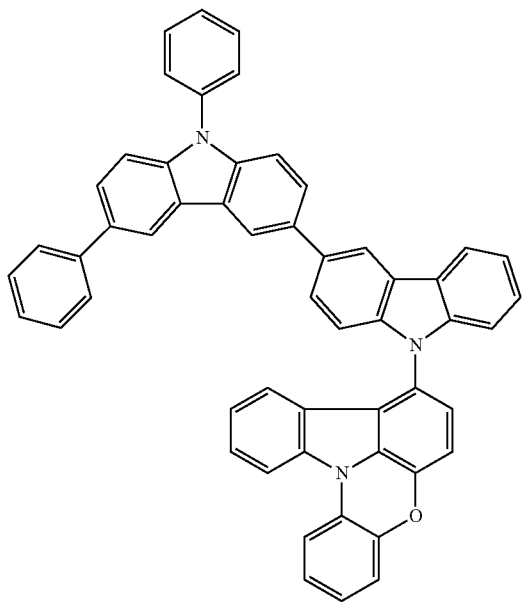

Synthesis Example 3: Synthesis of Compound 4

Compound 4 was synthesized in substantially the same manner as in Synthesis of Compound 8, except that the starting materials were appropriately changed. The structure of Compound 4 was identified using LC-MS. It was found that the molecular weight (m/z value) of Compound 4 measured by LC-MS was 908 (M+H$^+$), equal to the calculated molecular weight of Compound 4 ($C_{66}H_{41}N_3O_2$), 908.

4

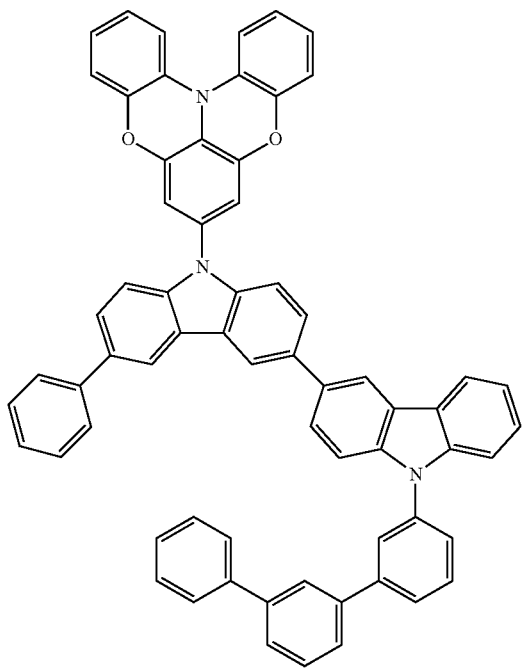

Example 1

PEDOT/PSS (available from Sigma-Aldrich Co., Ltd.) was coated on a glass substrate having an ITO anode to a thickness of 150 nanometers (nm) in stripe shape by spin coating to a thickness of 30 nm to form a dried film of a hole injection layer.

Then, a solution in which poly(9,9-dioctyl-fluorene-co-N-(4-butylphenyl)-diphenylamine) (TFB) was dissolved in xylene was coated on the hole injection layer by spin coating to a thickness of 30 nm to form a dried film of a hole transport layer.

Subsequently, a toluene solution including Compound 8 (as a host) and tris(2-(3-p-xylyl)phenyl)pyridine iridium (III) (as a dopant) was coated on the hole transport layer by spin coating to a thickness of 30 nm to form a dried film of an emission layer. Here, the amount of the dopant was 10% by weight based on the total weight of the emission layer.

Thereafter, the substrate having the emission layer thereon was mounted on a vacuum deposition apparatus, and Liq and KLET-03 were co-deposited on the emission layer to form an electron transport layer having a thickness of 50 nm.

An electron injection material (LiF) was deposited on the electron transport layer to form an electron injection layer having a thickness of 1 nm.

Subsequently, aluminum was deposited on the electron injection layer to form a cathode having a thickness of 100 nm, thereby completing the manufacture of an organic light-emitting device.

TFB is a polymer compound having a formula:

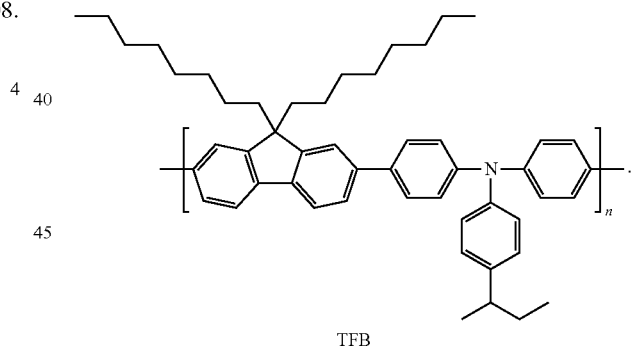

TFB

Example 2

An organic light-emitting device was manufactured in substantially the same manner as in Example 1, except that Compound 40 was used in place of Compound 8 to form an emission layer.

Example 3

An organic light-emitting device was manufactured in substantially the same manner as in Example 1, except that Compound A (ET-host) and Compound 4 were used at a weight ratio of 3:7 in place of Compound 8 to form an emission layer.

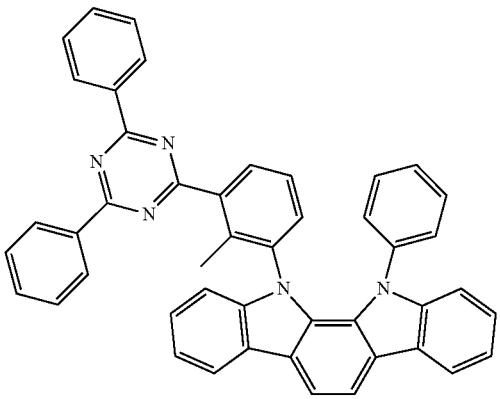

Comparative Example 1

An organic light-emitting device was manufactured in substantially the same manner as in Example 1, except that Compound B was used in place of Compound 8 to form an emission layer.

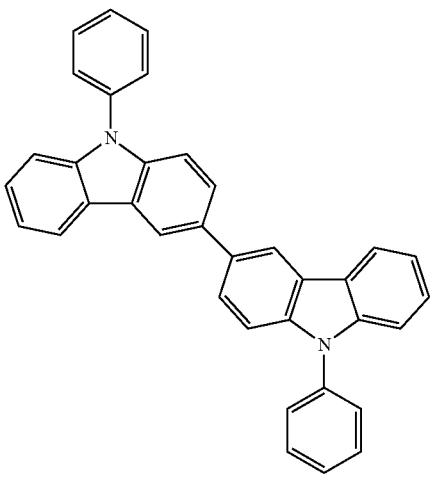

Evaluation Example

The current efficiency and luminous efficiency of the organic light-emitting devices manufactured in Examples 1 to 3 and Comparative Example 1 were evaluated in the following manner. A predetermined voltage was applied to each of the organic light-emitting devices by using a direct-current constant-voltage power source (for example, a source meter available from KEYENCE Co., Ltd.) for the emission of the organic light-emitting device. The luminance of each of the organic light-emitting device was measured by a luminance meter (for example, SR-3 available from Topcom Co., Ltd) while a current applied to the organic light-emitting device was gradually raised. Then, when the luminance reached 6,000 candelas per square meter (cd/m$^2$), the current was set to be constant, and the organic light-emitting device was stand for. The "driving voltage (V)" indicates the voltage at this point.

Then, a value of current per unit area (current density) of the organic light-emitting device was calculated, and the luminance (cd/m$^2$) was divided by the current density (amperes per square meter, A/m$^2$) to calculate "current efficiency (cd/A)".

In addition, the "emission lifespan (LT$_{80}$, hour)" indicates time (hour) for the luminance measured by the luminance meter to decline to 80% of its initial luminance.

The results of evaluation are shown in Table 1. The driving voltage, current efficiency, and emission lifespan are represented as relative to 100 of the measurement values of Comparative Example 1.

TABLE 1

| | Host material | Driving voltage | Current efficiency | Emission lifespan |
|---|---|---|---|---|
| Example 1 | Compound 8 | 87 | 160 | 230 |
| Example 2 | Compound 40 | 89 | 168 | 233 |
| Example 3 | Compound 4:Compound A (at a weight ratio of 7:3) | 85 | 186 | 367 |
| Comparative Example 1 | Compound B | 100 | 100 | 100 |

Referring to Table 1, it was found that the organic light-emitting devices of Example 1 to 3 have lower driving voltage, higher current efficiency, and longer luminescence lifespan than the organic light-emitting device of Comparative Example 1.

According to one or more embodiments, a bicarbazole compound may include at least one group represented by Formula 1A and at least one specified group represented by Formula 1B. When the bicarbazole compound represented by Formula 1 is used as a hole transport host material, the driving voltage of the organic light-emitting device may be lowered, and the emission lifespan and luminous efficiency may improve. In addition, since the bicarbazole compound represented by Formula 1 may have excellent solubility in a solvent and may be an excellent material for forming films by coating, an organic light-emitting device having excellent efficiency may be manufactured by solution coating.

Also, the range of application of the bicarbazole compound according to an embodiment is not limited to a hole transport host material. The bicarbazole compound represented by Formula 1 may be used, for example, as a hole transport material, in a charge transport layer, as a bipolar type host material, or as an electron transport host material by changing a substituent.

As apparent from the foregoing description, an organic light-emitting device according to one or more embodiments may have low driving voltage, excellent current efficiency, and long lifespan.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the present disclosure as defined by the following claims.

What is claimed is:
1. A bicarbazole compound represented by Formula 1:
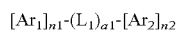    Formula 1
wherein, in Formula 1,
Ar₁ is represented by one of Formulae 1-1, 1-2, and 1-4 to 1-21:
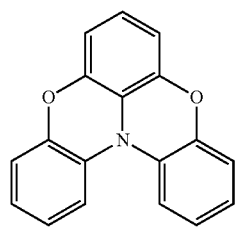
1-1
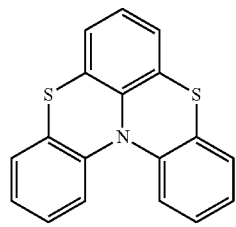
1-2
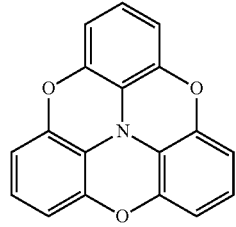
1-4
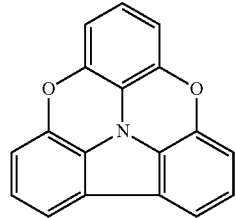
1-5
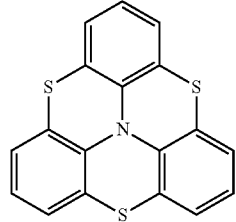
1-6
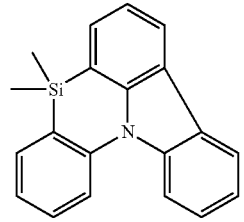
1-7
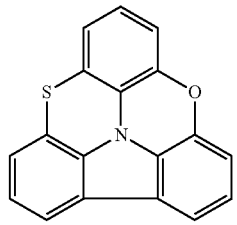
1-8
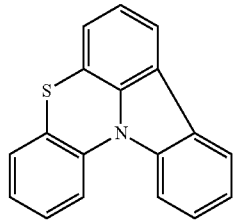
1-9
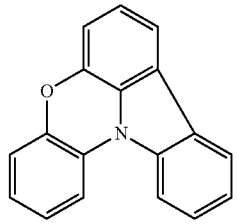
1-10
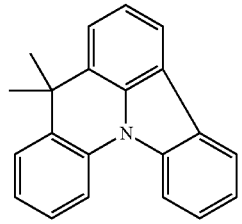
1-11
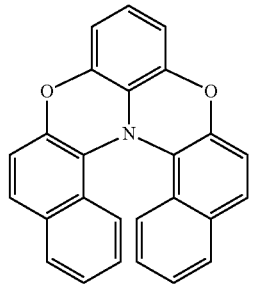
1-12
1-13

-continued 1-14
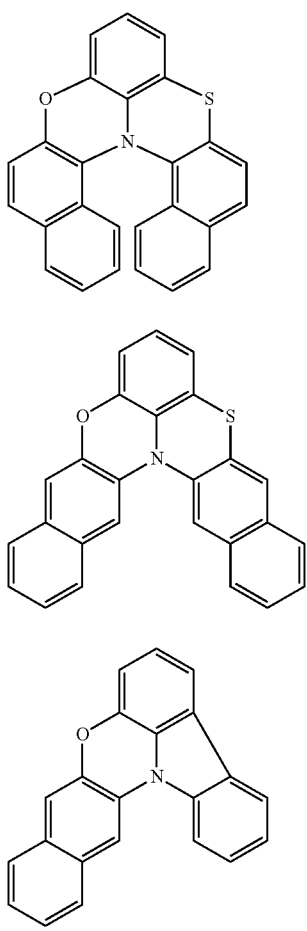

1-15

1-16

1-17

1-18

-continued 1-19
1-20
1-21

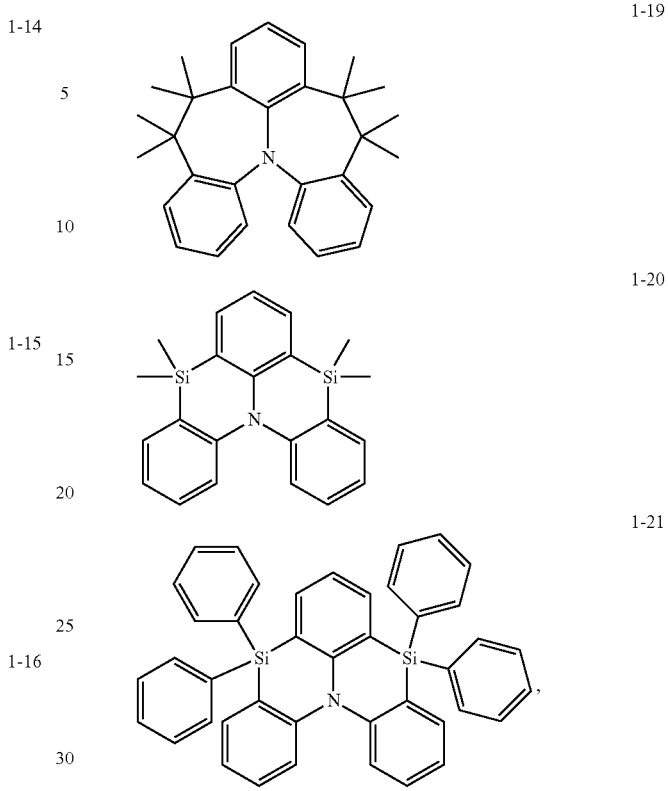

wherein, in Formulae 1-1, 1-2, and 1-4 to 1-21,
at least one hydrogen is substituted with a group serving as a binding site to $L_1$, $Ar_2$ is represented by Formula 1B:

Formula 1B

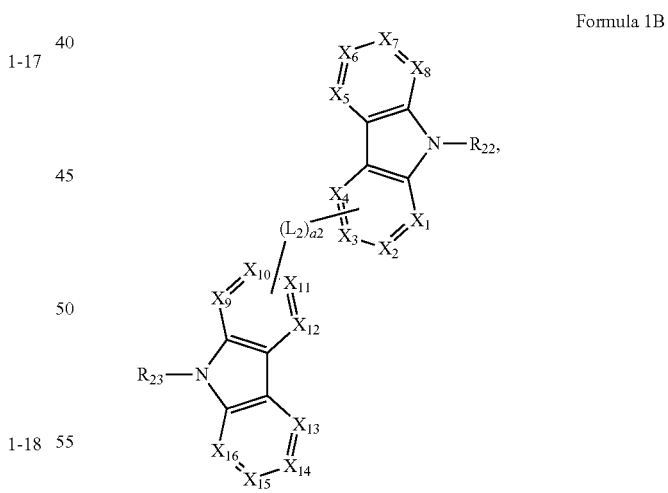

wherein, in Formula 1B,
$X_1$ to $X_{16}$ are each independently selected from a nitrogen atom and $CR_{21}$,
$R_{21}$ is selected from a binding site to $L_1$, a binding site to $L_2$, hydrogen, a deuterium atom, a substituted or unsubstituted $C_1$-$C_{10}$ alkyl group, a substituted or unsubstituted aryl group comprising 6 to 30 ring-forming atoms, and a substituted or unsubstituted heteroaryl group comprising 5 to 30 ring-forming atoms,

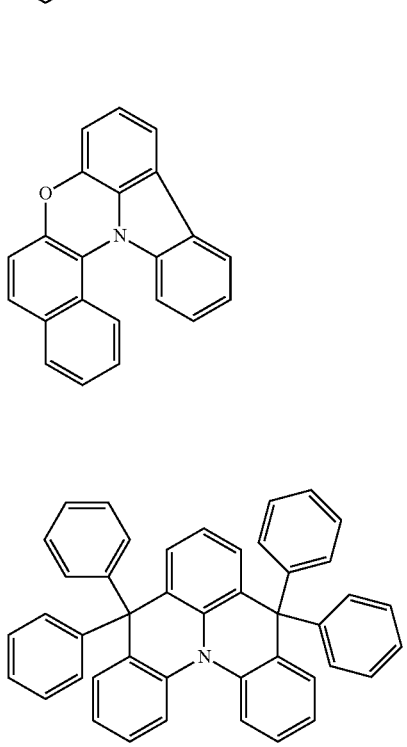

R$_{21}$ is optionally bound to adjacent R$_{21}$ to form a condensed ring, two substituents of X$_1$ to X$_{16}$ each comprises a C-(L$_2$-binding site) structure, R$_{22}$ and R$_{23}$ are each independently selected from a binding site to L$_1$, a substituted or unsubstituted aryl group comprising 6 to 30 ring-forming atoms, and a substituted or unsubstituted heteroaryl group comprising 5 to 30 ring-forming atoms, at least one selected from R$_{21}$ to R$_{23}$ is a binding site to L$_1$, n1 and n2 are each independently an integer from 1 to 20, L$_1$ and L$_2$ are each independently selected from a single bond and a substituted or unsubstituted arylene group comprising 6 to 30 ring-forming atoms, and a1 and a2 are each independently an integer from 0 to 3.

2. The bicarbazole compound of claim 1, wherein

X$_1$ to X$_{16}$ are CR$_{21}$,

R$_{21}$ are each independently selected from a binding site to L$_1$, a binding site to L$_2$, hydrogen, a substituted or unsubstituted aryl group comprising 6 to 30 ring-forming atoms, and a substituted or unsubstituted heteroaryl group comprising 5 to 30 ring-forming atoms, and at least two substituents selected from X$_1$ to X$_{16}$ is C, which is a binding site to L$_2$.

3. The bicarbazole compound of claim 1, wherein R$_{22}$ and R$_{23}$ are each independently selected from a binding site to L$_1$, a phenyl group, a naphthyl group, an anthracenyl group, a phenanthrenyl group, a biphenyl group, a terphenyl group, a fluoranthenyl group, a fluorenyl group, a pyrrolyl group, a pyridinyl group, a pyrazinyl group, a triazinyl group, a furanyl group, a benzofuranyl group, an isobenzofuranyl group, a quinolyl group, an isoquinolyl group, a quinoxalinyl group, a carbazolyl group, a furazanyl group, a thienyl group, a benzothienyl group, a dibenzofuranyl group, a dibenzothienyl group, and groups represented by Formula 1A.

4. The bicarbazole compound of claim 1, wherein X$_3$ and X$_{11}$ are each C, which is a binding site to L$_2$.

5. The bicarbazole compound of claim 1, wherein

X$_3$ is C, which is a binding site to L$_1$,

X$_6$ is C, which is a binding site to L$_1$,

X$_{11}$ is C, which is a binding site to L$_1$,

X$_{14}$ is C, which is a binding site to L$_1$,

R$_{22}$ is a binding site to L$_1$, or

R$_{23}$ is a binding site to L$_1$.

6. The bicarbazole compound of claim 1, wherein n1 and n2 are each independently selected from 1, 2, 3, 4, and 5.

7. The bicarbazole compound of claim 1, wherein L$_1$ and L$_2$ are each independently a single bond.

8. The bicarbazole compound of claim 1, wherein a1 and a2 are each independently selected from 0 and 1.

9. The bicarbazole compound of claim 1 selected from Compounds 1 to 58:

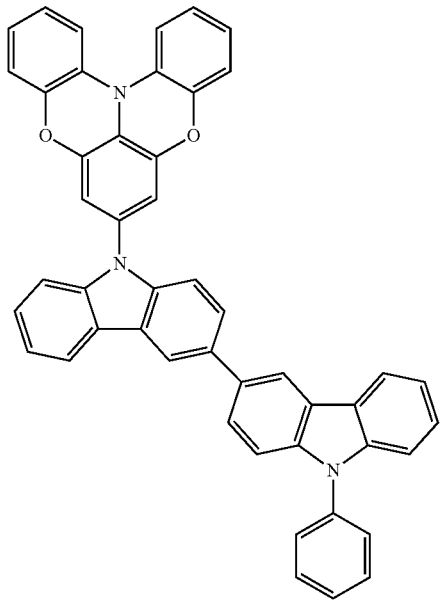

1

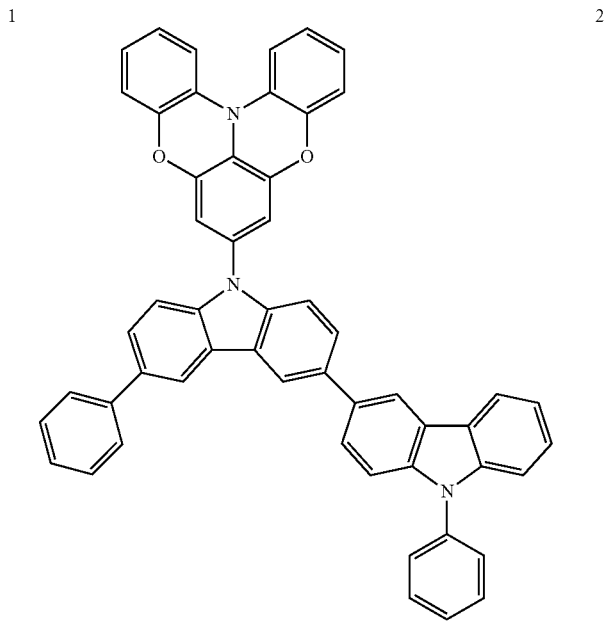

2

3
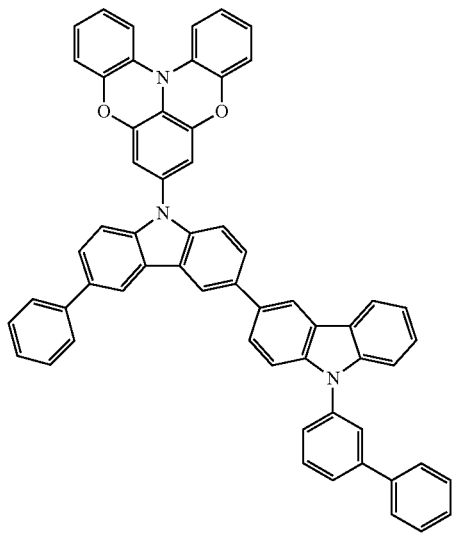
4
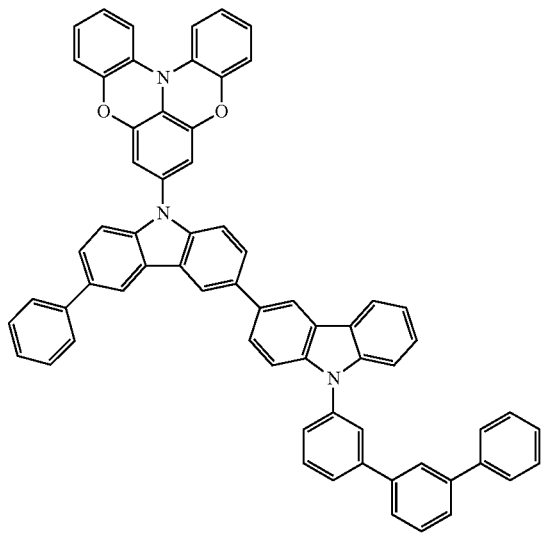
5
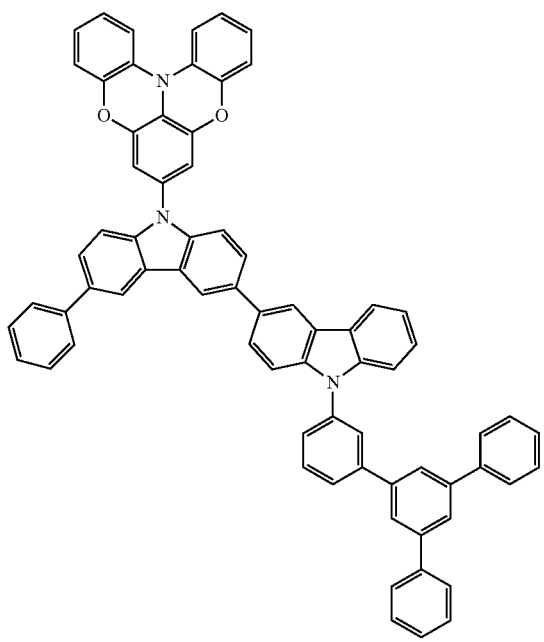
6
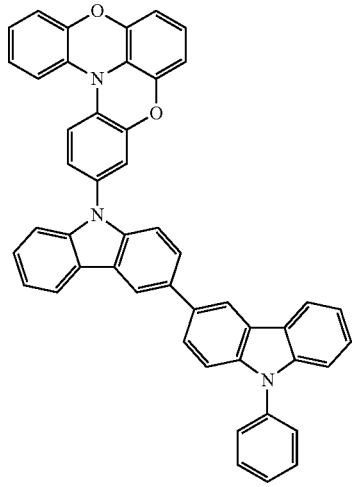

-continued
7
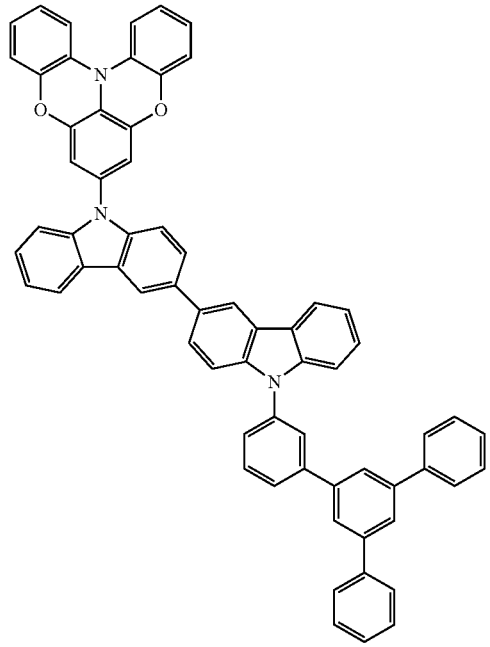
8
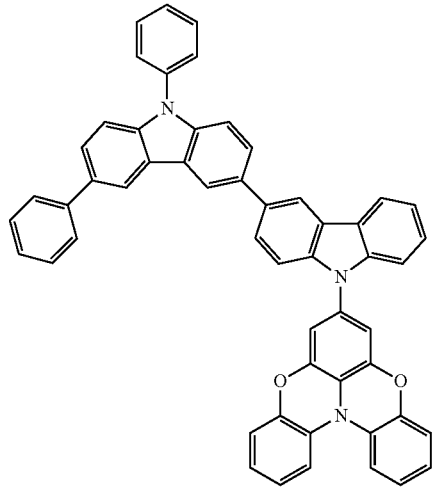
9
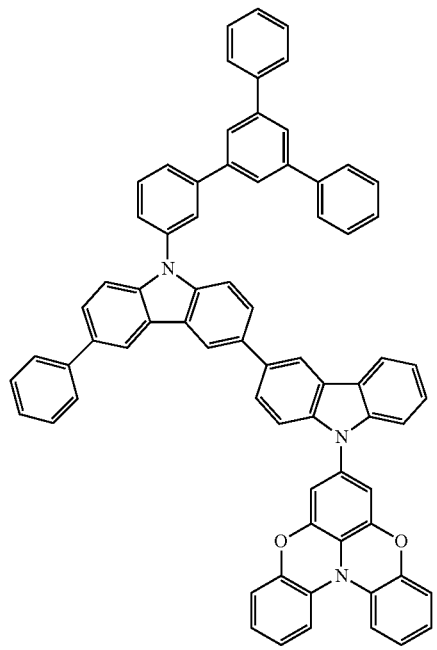
10
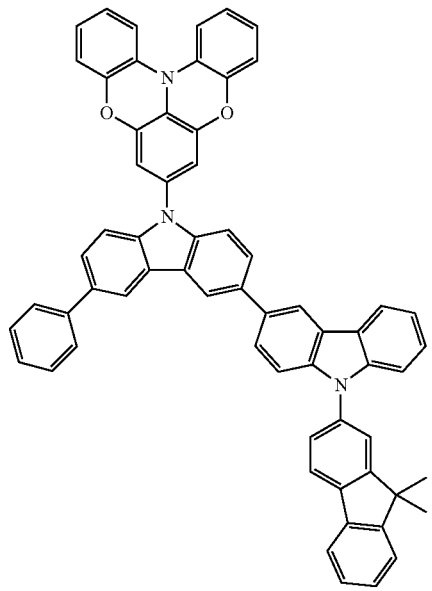

-continued
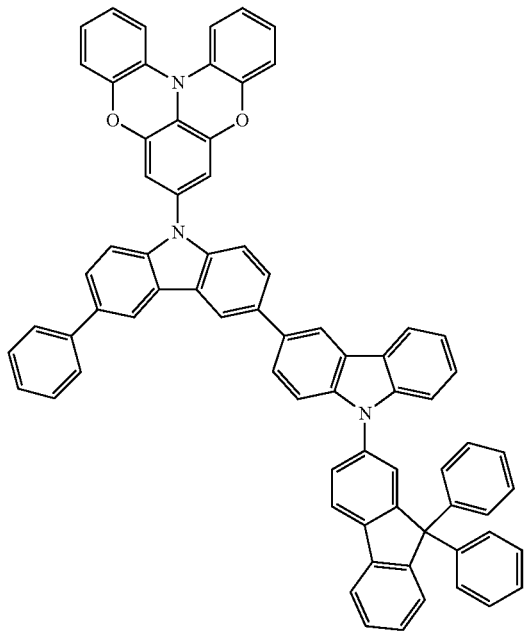
11
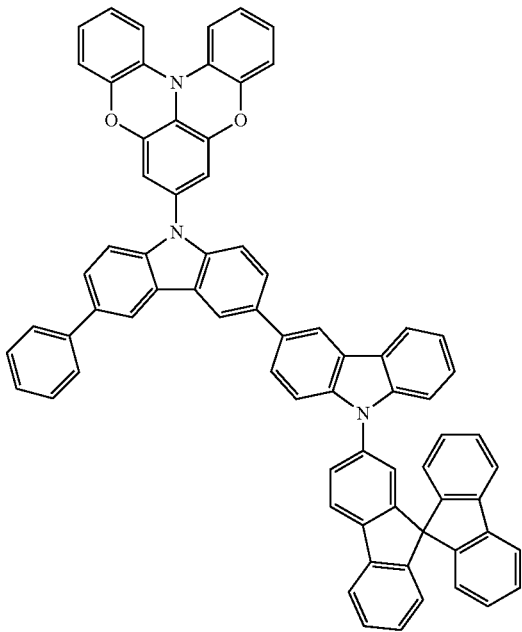
12
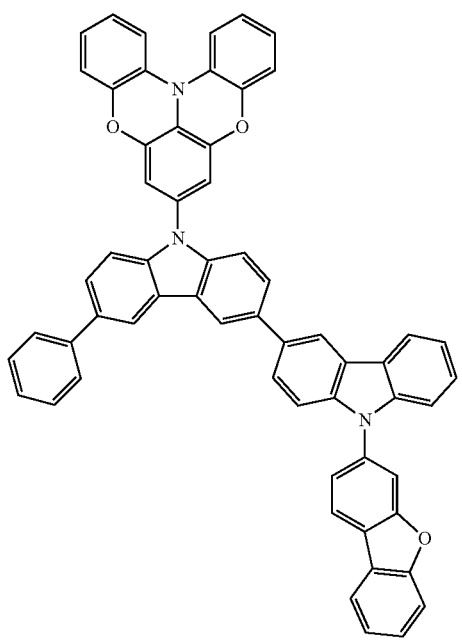
13
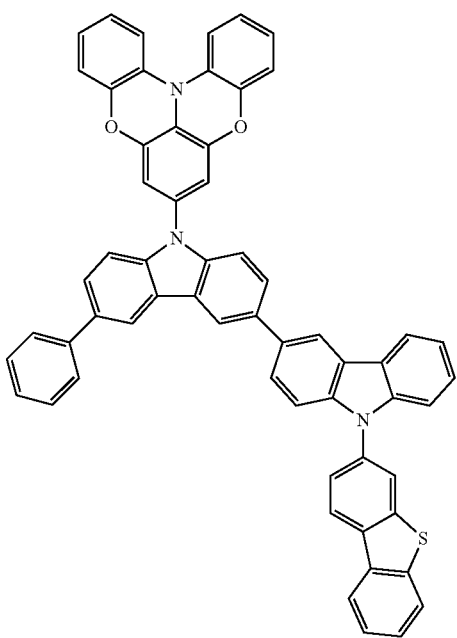
14

-continued
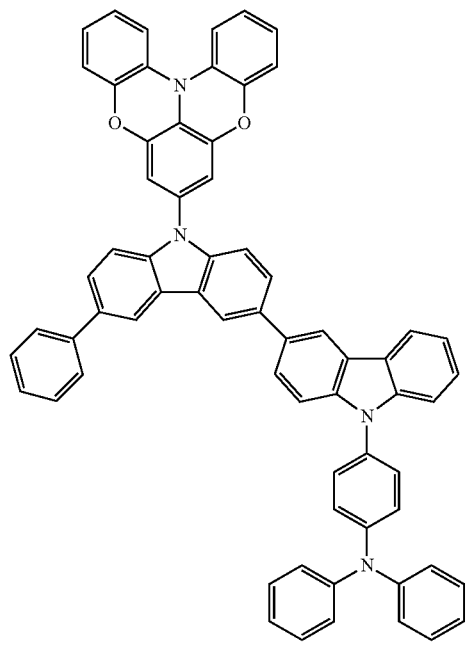
15
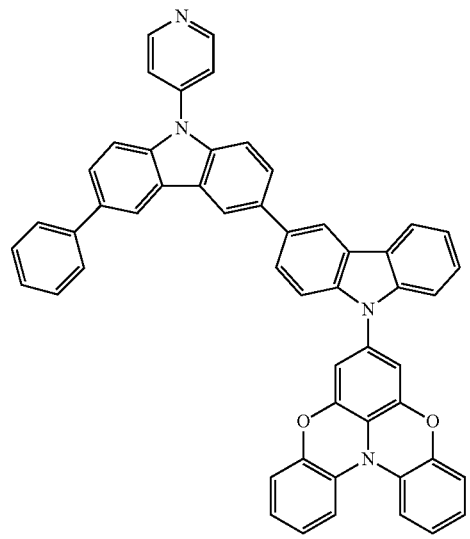
16
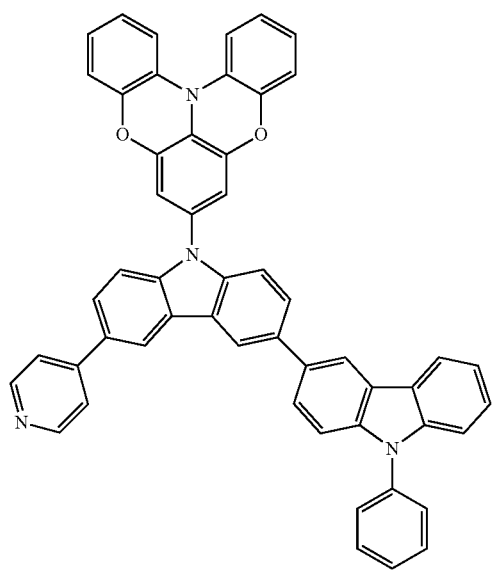
17
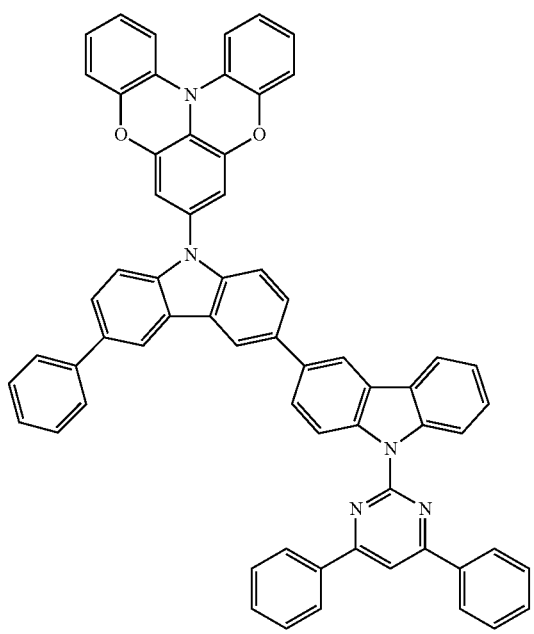
18

19
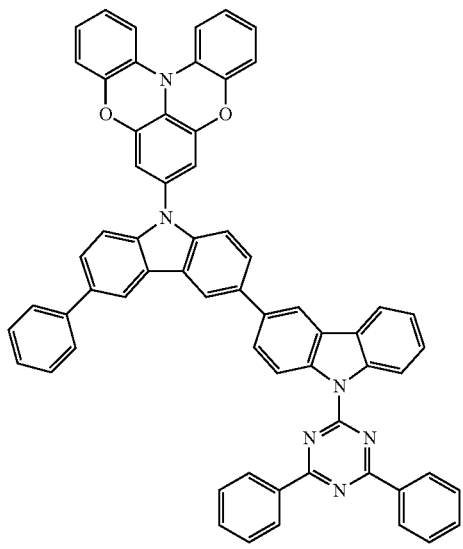
20
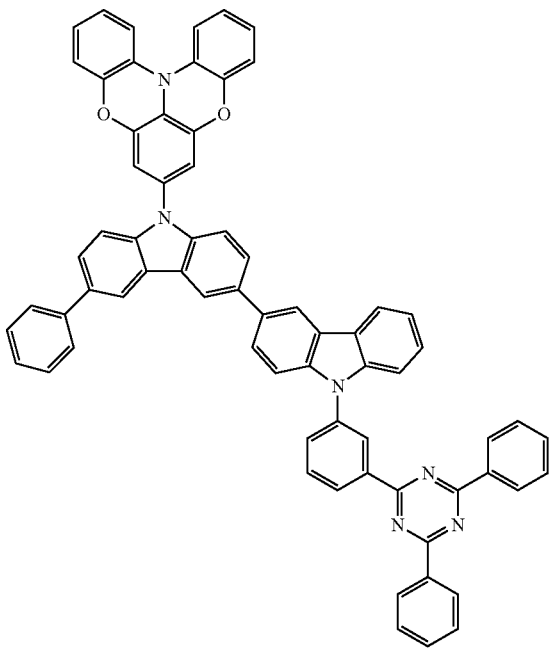
21
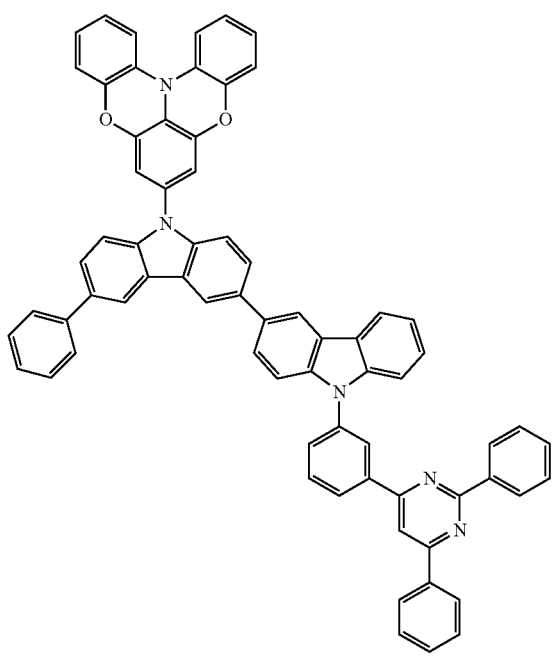
22
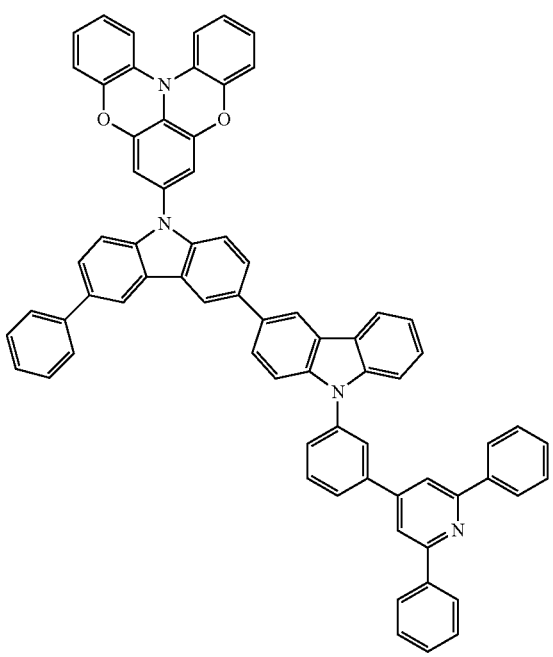

-continued
23
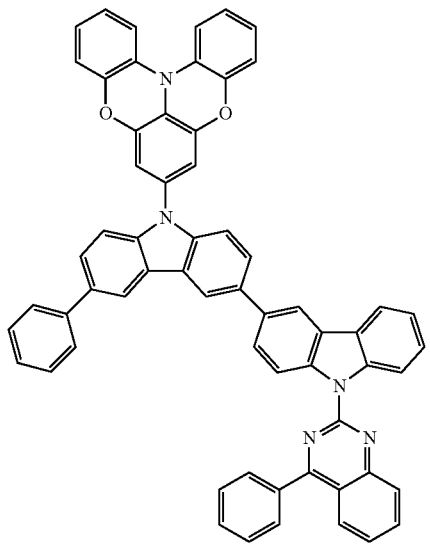
24
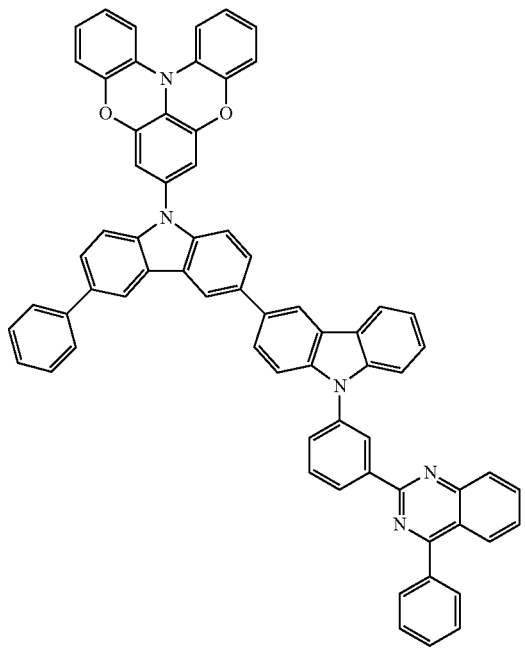
25
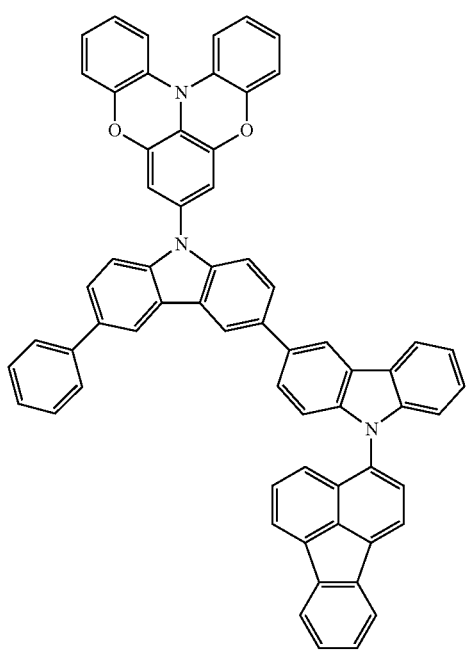
26
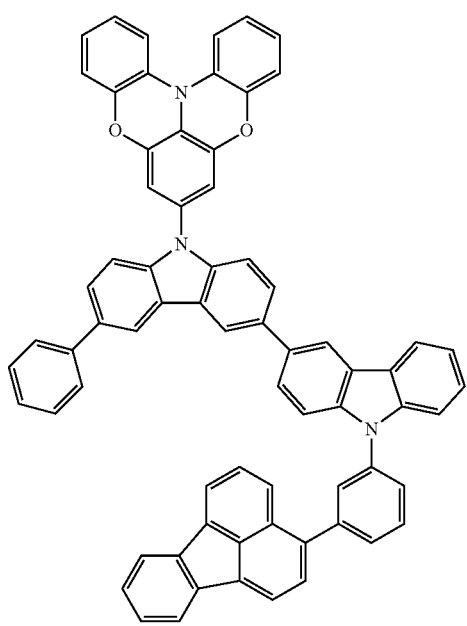

-continued
27
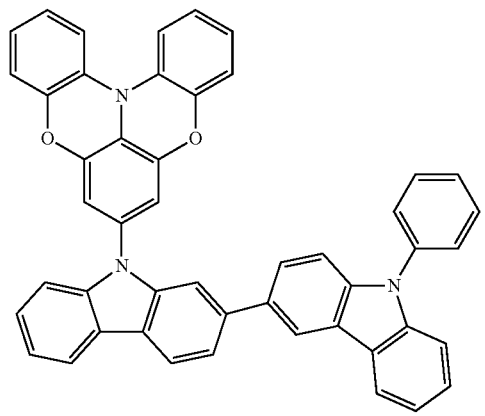
28
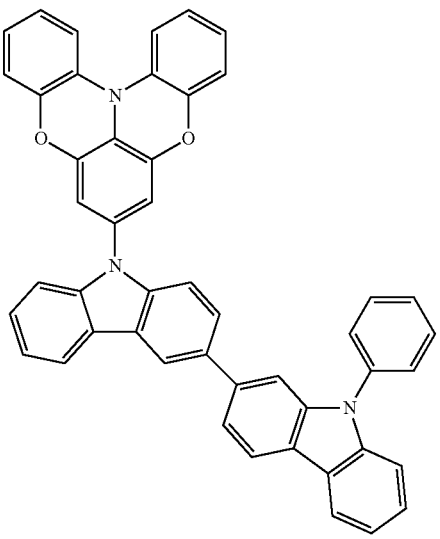
29
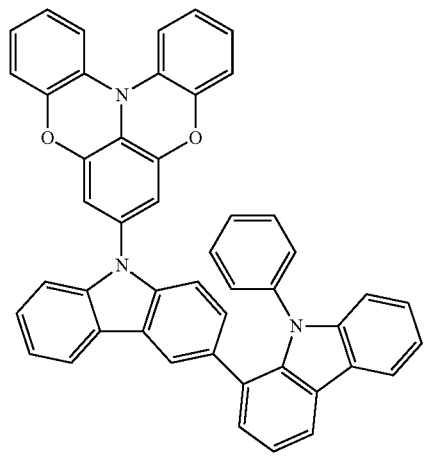
30
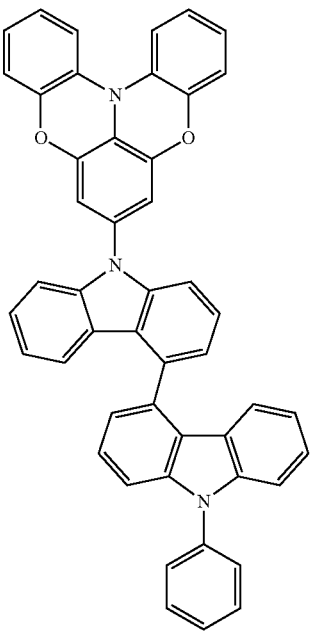

-continued
31
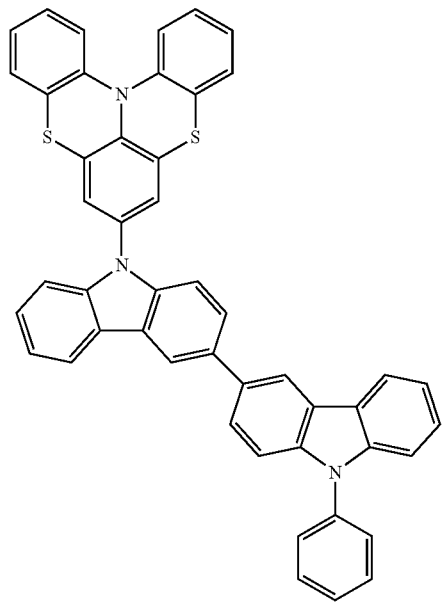
32
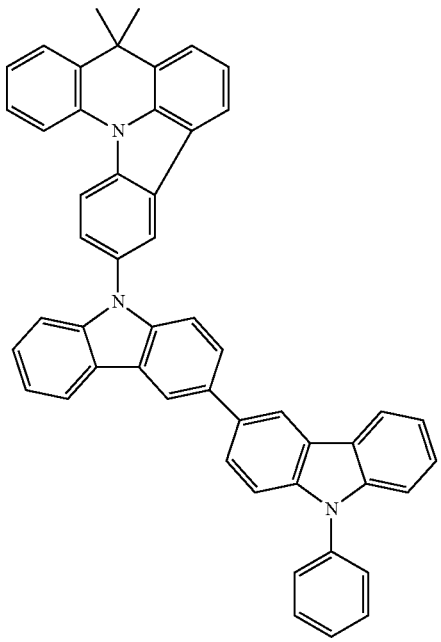
33
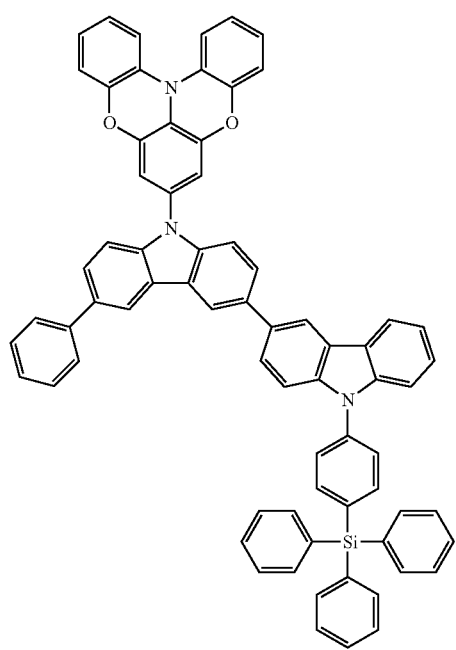
34
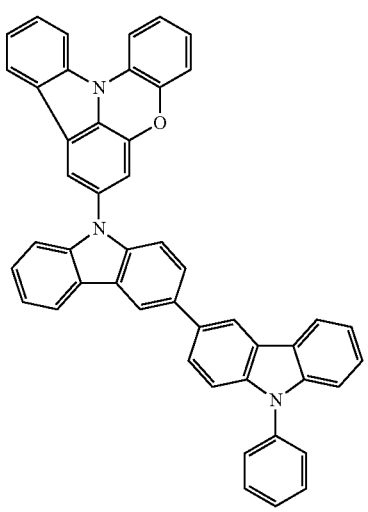

-continued
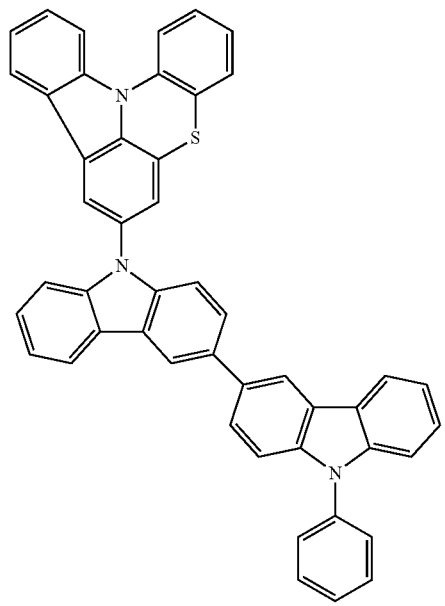
35
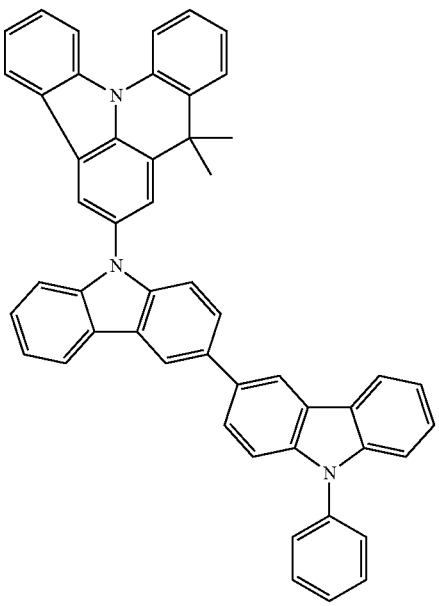
36
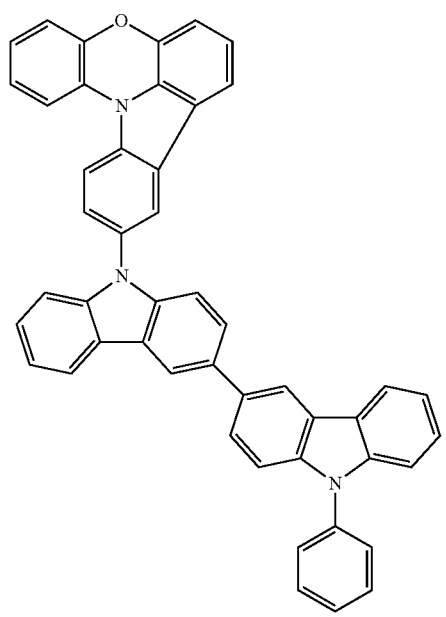
37
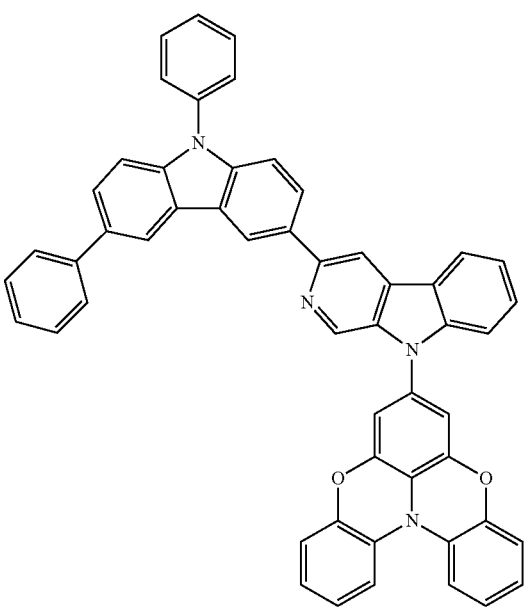
38

39
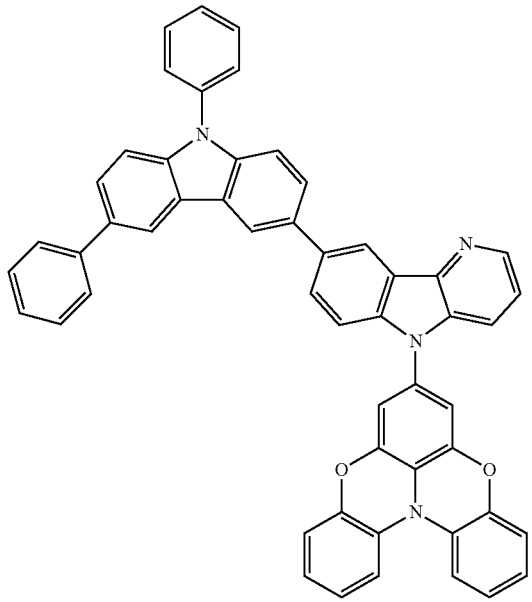
40
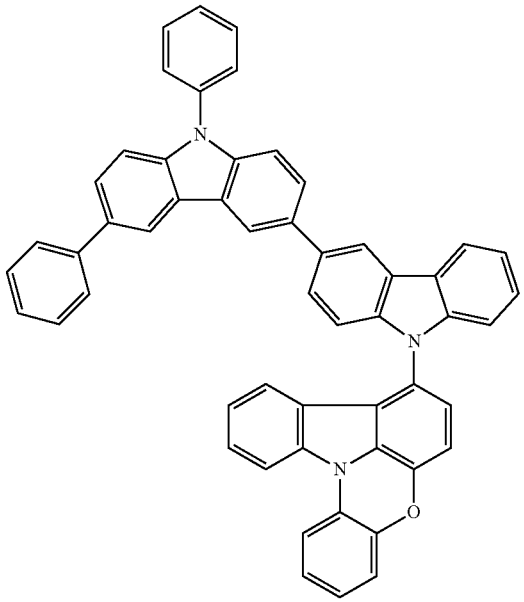
41
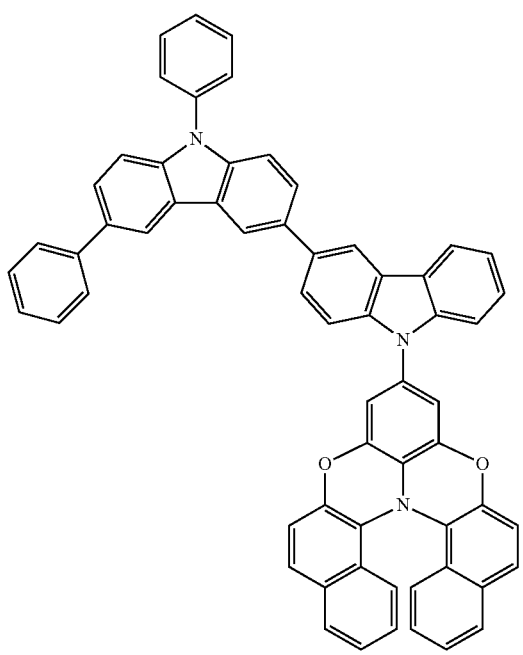
42
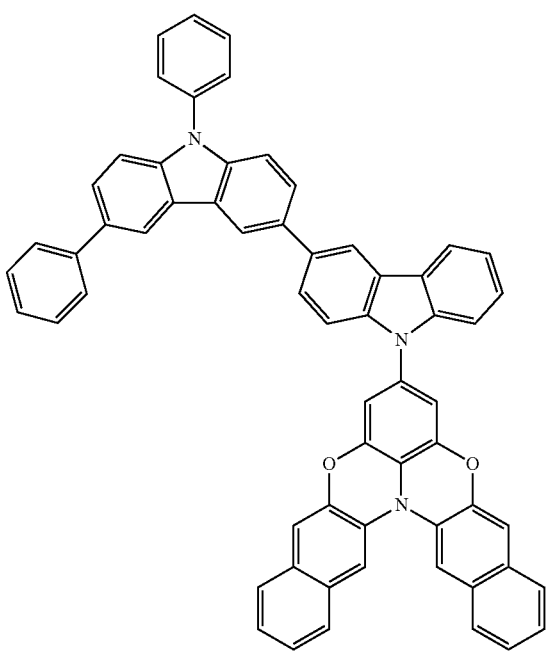

-continued
43
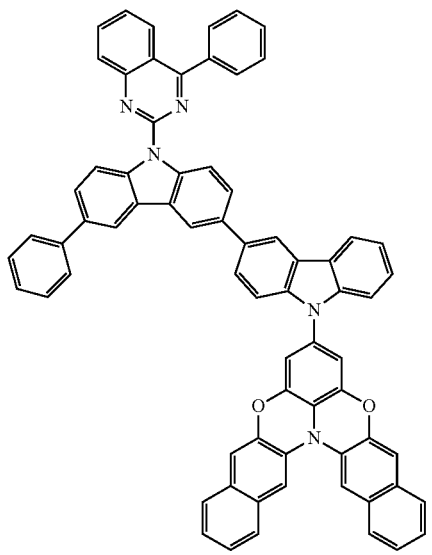
44
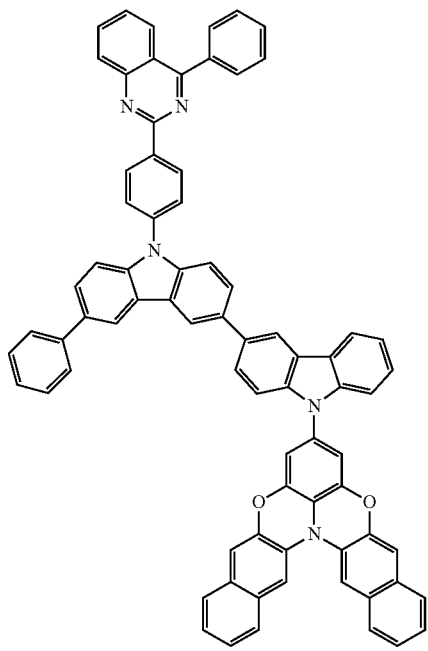
45
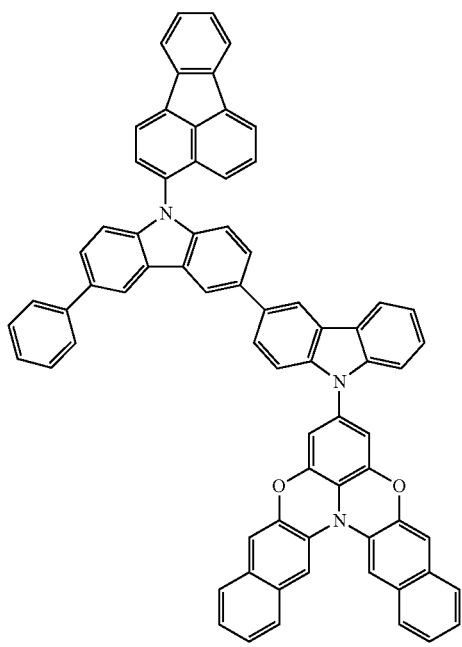
46
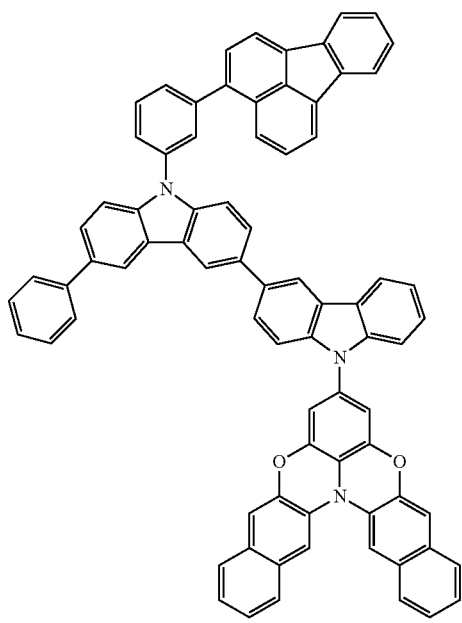

47
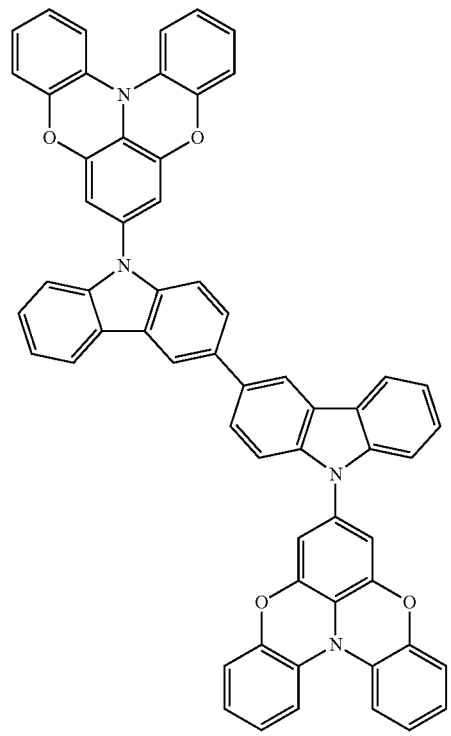
48
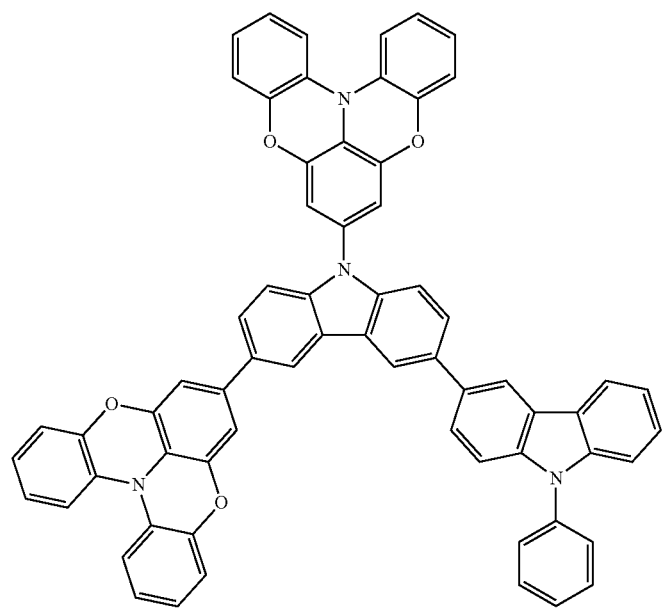

-continued
49
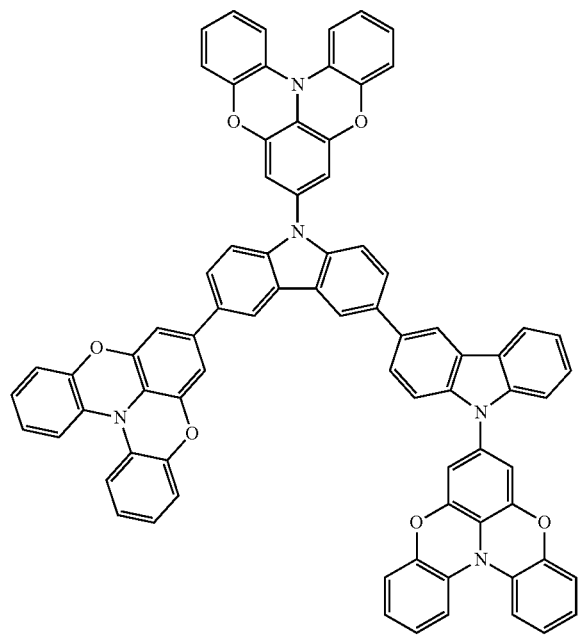
50
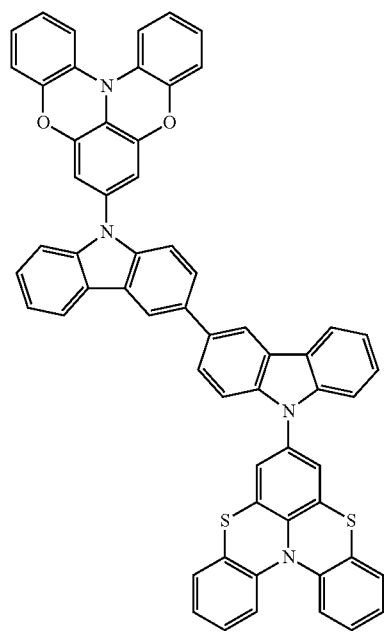
51
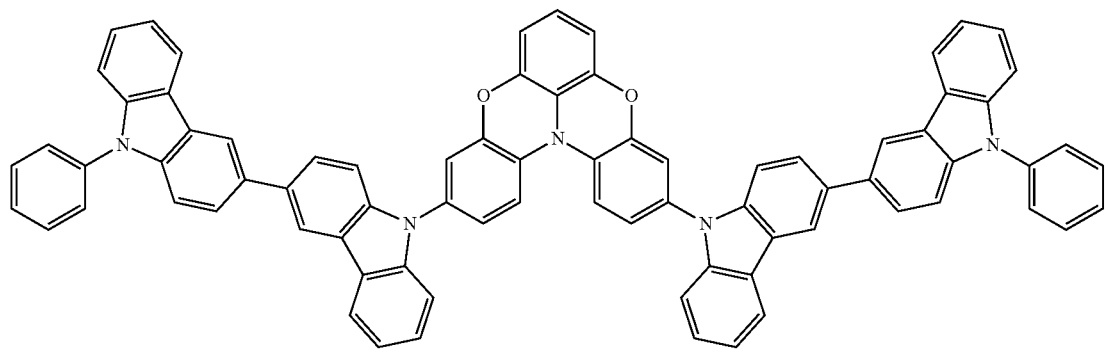

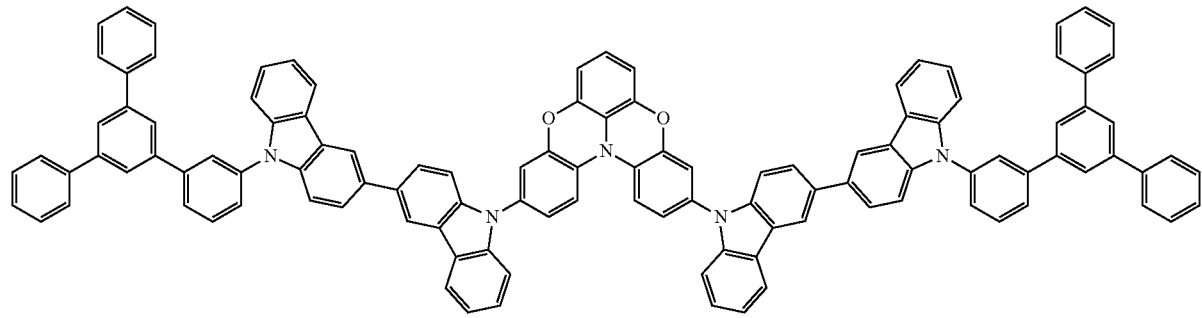
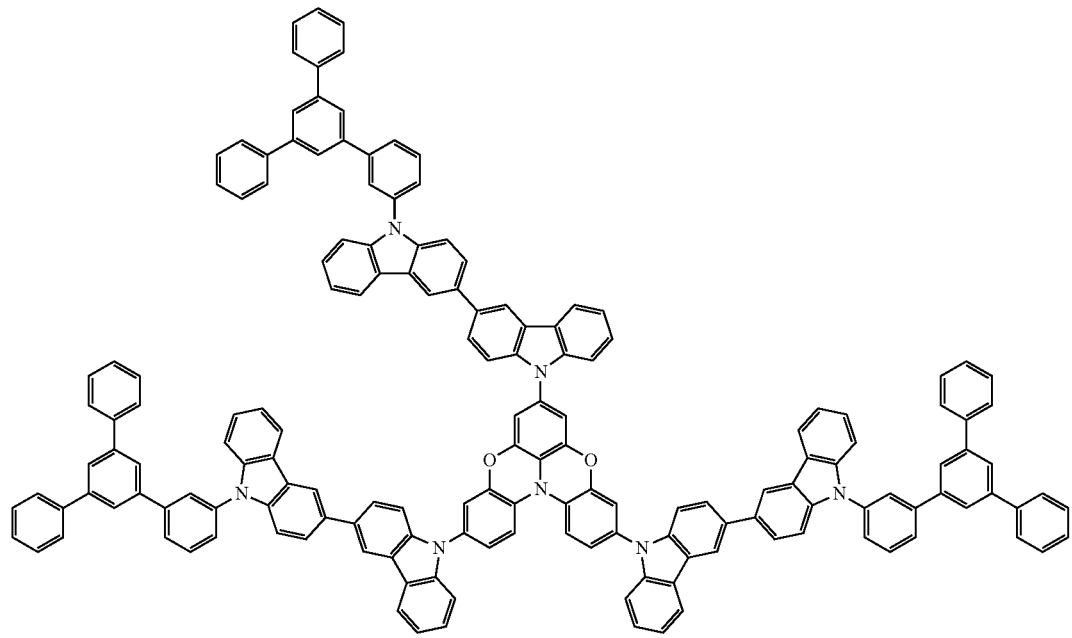
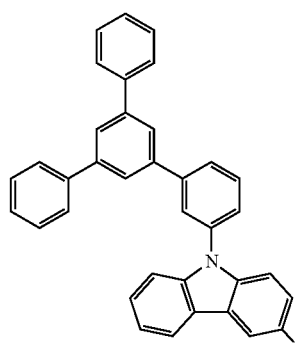

-continued
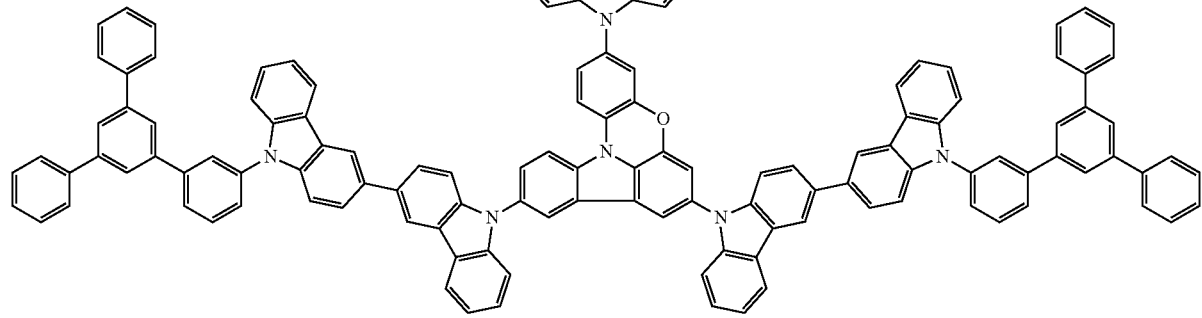
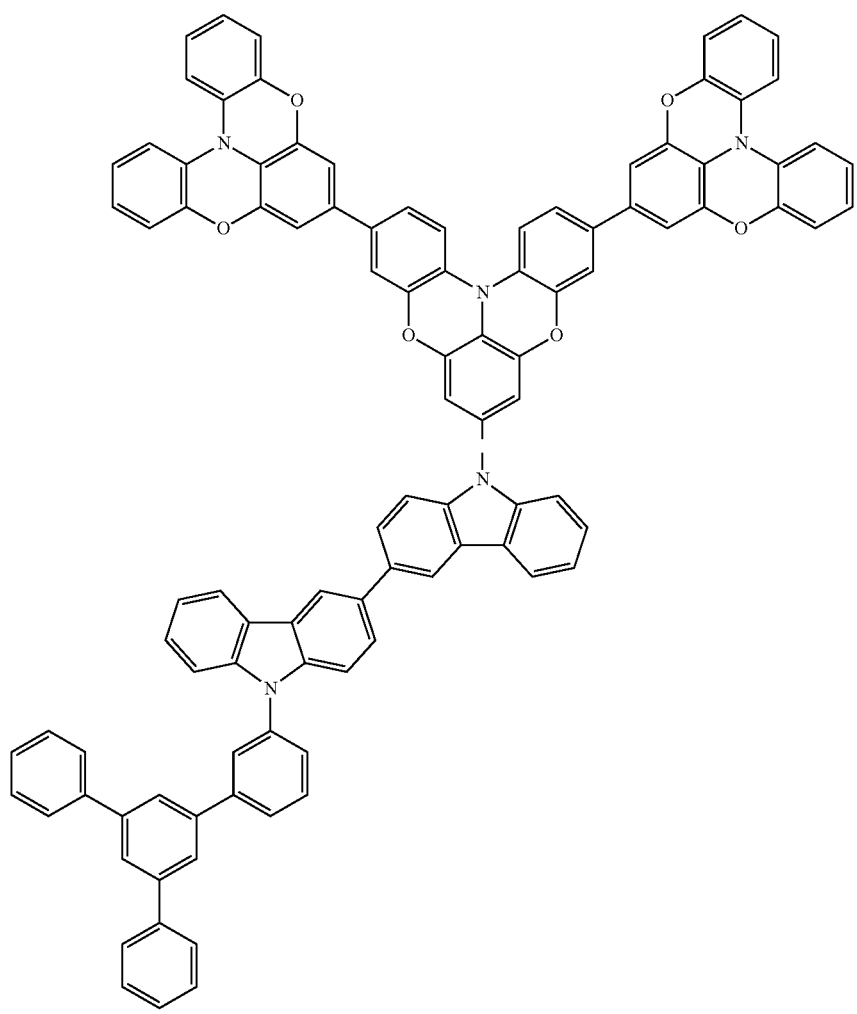

-continued
56
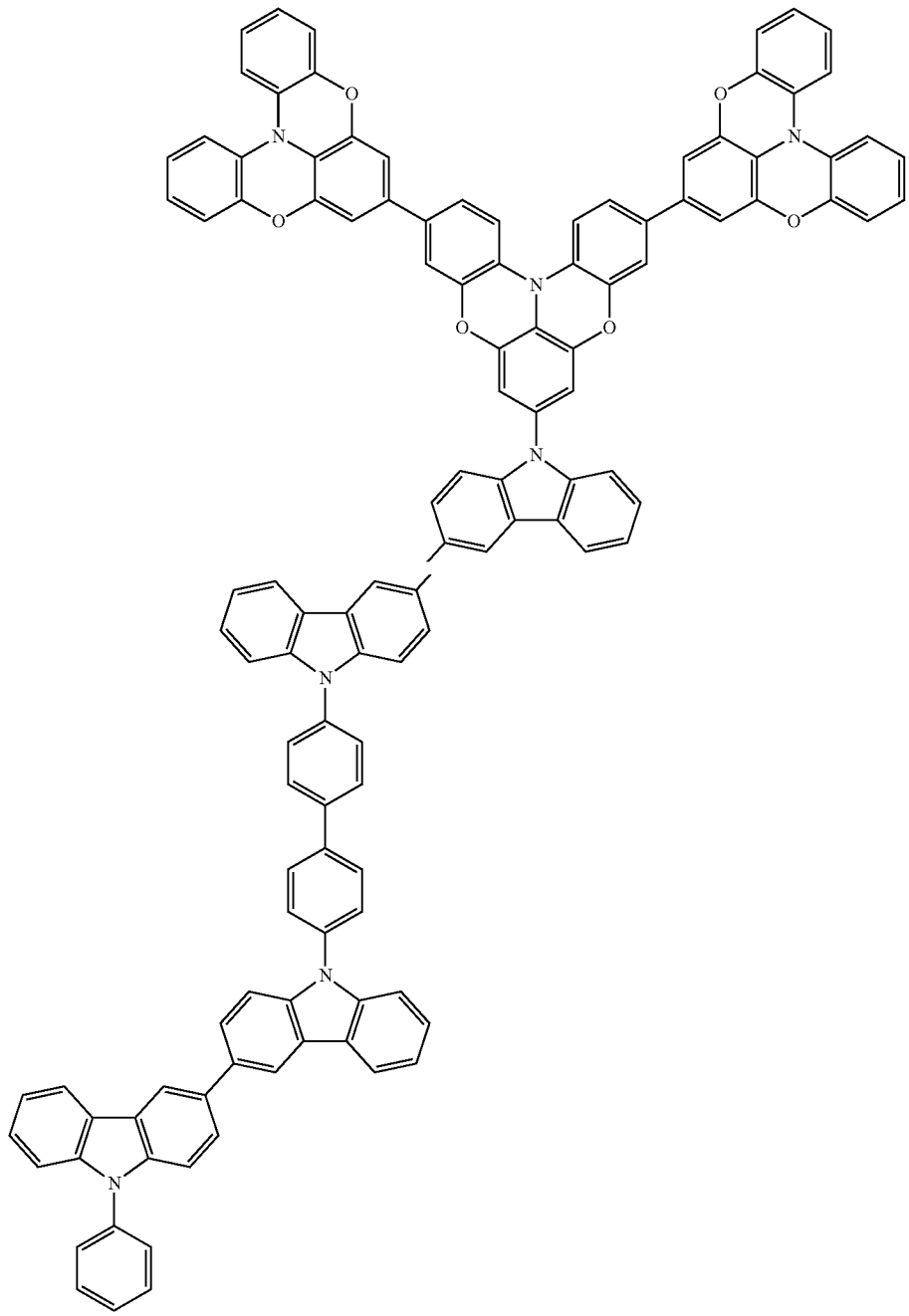

57
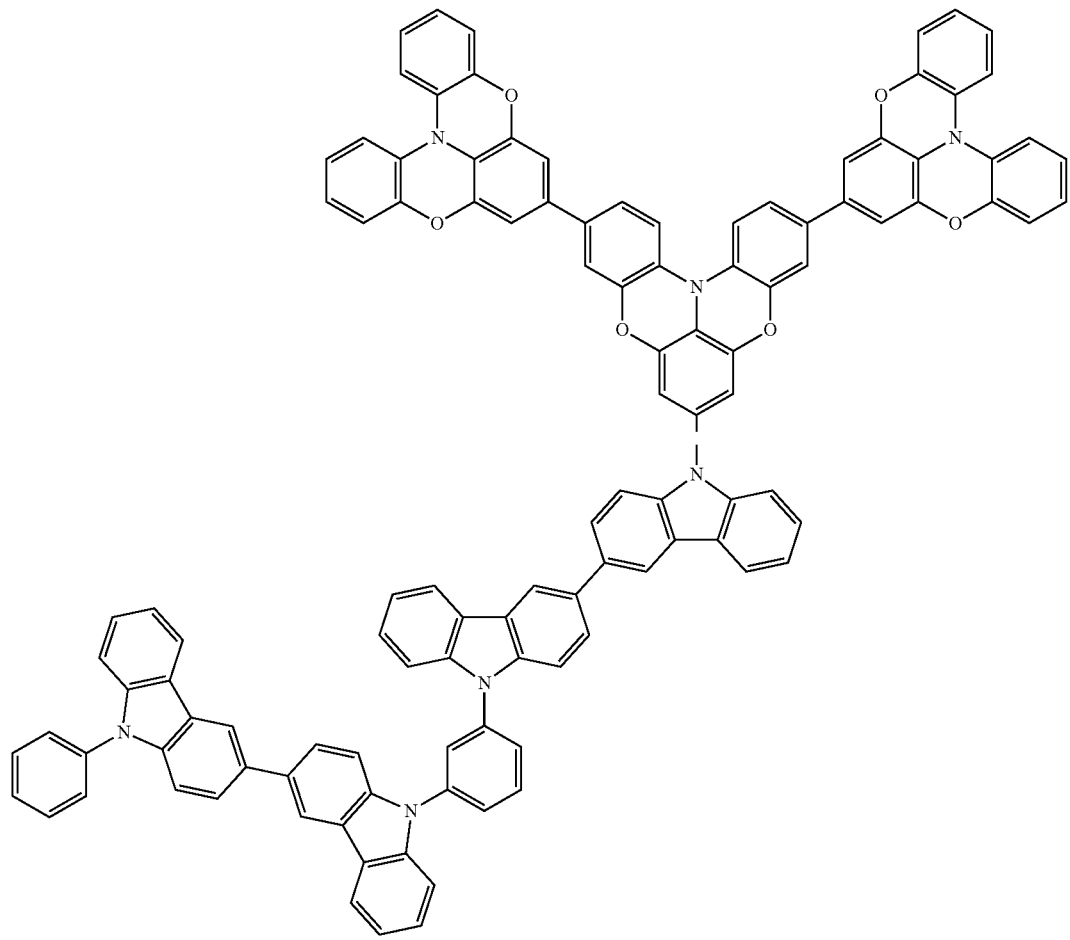
58
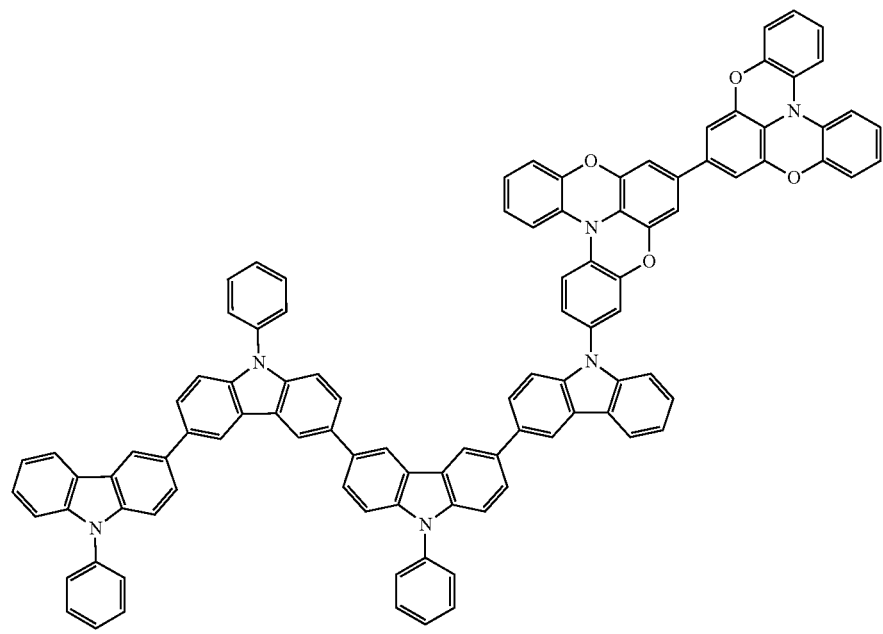

10. A material for an organic light-emitting device comprising at least one bicarbazole compound represented by Formula 1 of claim 1.

11. The material of claim 10 further comprising a solvent.

12. An organic light emitting device comprising:
a first electrode;
a second electrode; and
an organic layer disposed between the first electrode and the second electrode,
wherein the organic layer comprises an emission layer and at least one bicarbazole compound represented by Formula 1 of claim 1.

13. The organic light-emitting device of claim 12, wherein the organic layer further comprises an emission material, and
the emission material emits light from triplet excitons.

* * * * *